(12) United States Patent
Kawabata et al.

(10) Patent No.: US 10,792,017 B2
(45) Date of Patent: Oct. 6, 2020

(54) ULTRASOUND DIAGNOSTIC APPARATUS, ULTRASOUND DIAGNOSTIC IMAGE GENERATING METHOD, AND PROGRAM

(71) Applicant: Konica Minolta, Inc., Tokyo (JP)

(72) Inventors: Akihiro Kawabata, Hachioji (JP); Masashi Kunita, Yokohama (JP); Shinya Kurokawa, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 483 days.

(21) Appl. No.: 15/692,529

(22) Filed: Aug. 31, 2017

(65) Prior Publication Data

US 2018/0070924 A1 Mar. 15, 2018

(30) Foreign Application Priority Data

Sep. 13, 2016 (JP) .................................. 2016-178282

(51) Int. Cl.
*A61B 8/08* (2006.01)
*G01S 15/89* (2006.01)
(Continued)

(52) U.S. Cl.
CPC .............. *A61B 8/5238* (2013.01); *A61B 8/14* (2013.01); *A61B 8/5246* (2013.01); *G01S 15/89* (2013.01);
(Continued)

(58) Field of Classification Search
CPC ....... A61B 8/5238; A61B 8/5246; A61B 8/14; A61B 8/0866; A61B 8/466; A61B 8/58;
(Continued)

(56) References Cited

U.S. PATENT DOCUMENTS 5,476,097 A * 12/1995 Robinson ................. A61B 8/06
600/441
5,709,210 A * 1/1998 Green .................. A61B 5/0456
600/453
(Continued)

FOREIGN PATENT DOCUMENTS

JP 2008142130 A 6/2008

*Primary Examiner* — Oommen Jacob
(74) *Attorney, Agent, or Firm* — Lucas & Mercanti, LLP

(57) ABSTRACT

An ultrasound diagnostic apparatus that can combine image data and has a first image mode and a second image mode, includes: a hardware processor that sets a scan parameter of an image of a first image mode according to restriction information of the scan parameter, when the second image mode is turned on and generates control information; a transmitter that generates a drive signal and inputs the drive signal to an ultrasound probe that transmits transmission ultrasound to a test object and receives reflected ultrasound; a receiver that generates a reception signal of the images in the first and second image modes from an electric signal generated in the ultrasound probe; a first-image-mode image generator that generates first-image-mode image data; a second-image-mode image generator that generates second-image-mode image data; and a combiner that generates combined image data by combining the generated first-image-mode image data and second-image-mode image data.

21 Claims, 12 Drawing Sheets

(51) Int. Cl.
*A61B 8/14* (2006.01)
*A61B 8/00* (2006.01)

(52) U.S. Cl.
CPC ............ *A61B 8/0866* (2013.01); *A61B 8/466* (2013.01); *A61B 8/58* (2013.01)

(58) Field of Classification Search
CPC .. G01S 15/89; G01S 7/52098; G01S 7/52038; G01S 15/8997; G01S 15/8963; G01S 7/52085
USPC .................................................. 600/437, 407
See application file for complete search history.

(56) References Cited

U.S. PATENT DOCUMENTS

| | | | | |
|---|---|---|---|---|
| 5,913,823 | A * | 6/1999 | Hedberg | A61B 8/08 600/443 |
| 5,967,985 | A * | 10/1999 | Hayakawa | A61B 8/0833 600/440 |
| 6,176,830 | B1 * | 1/2001 | Freiburger | A61B 8/06 600/453 |
| 6,450,961 | B1 * | 9/2002 | Shiki | A61B 8/06 600/458 |
| 7,951,085 | B2 * | 5/2011 | Lee | A61B 8/06 600/437 |
| 8,216,141 | B2 * | 7/2012 | Ahn | G01S 7/52025 600/437 |
| 9,173,630 | B2 * | 11/2015 | Kanda | A61B 8/08 |
| 9,322,902 | B2 * | 4/2016 | Ahn | G01S 7/52025 |
| 9,538,990 | B2 * | 1/2017 | Baba | A61B 8/06 |
| 10,342,515 | B2 * | 7/2019 | Loupas | A61B 8/06 |
| 10,433,813 | B2 * | 10/2019 | Takimoto | G01S 15/8988 |
| 2003/0028107 | A1 * | 2/2003 | Miller | A61B 5/6819 600/437 |
| 2003/0045795 | A1 * | 3/2003 | Bjaerum | G01S 7/52034 600/441 |
| 2005/0203401 | A1 * | 9/2005 | Takimoto | A61B 8/06 600/441 |
| 2006/0100515 | A1 * | 5/2006 | Nakata | A61B 8/06 600/441 |
| 2007/0078347 | A1 * | 4/2007 | Srinivasan | A61B 8/06 600/465 |
| 2007/0239015 | A1 * | 10/2007 | Sato | G01S 7/52085 600/454 |
| 2010/0240992 | A1 * | 9/2010 | Hao | A61B 8/585 600/437 |
| 2014/0039317 | A1 * | 2/2014 | Sato | A61B 8/54 600/443 |
| 2018/0070924 | A1 * | 3/2018 | Kawabata | G01S 15/8997 |

\* cited by examiner

FIG. 3

| MENU DESCRIPTION | DENSITY RESTRICTION | THI RESTRICTION | MULTIPLE FOCUSING RESTRICTION | SYNTHETIC APERTURE RESTRICTION |
|---|---|---|---|---|
| OFF | NONE (SH) | NONE (THI ON) | NONE (ON) | NONE (ON) |
| A1 | NONE (SH) | NONE (THI ON) | OFF | OFF |
| A2 | UH | NONE (THI ON) | OFF | OFF |
| A3 | H | NONE (THI ON) | OFF | OFF |
| A4 | M | NONE (THI ON) | OFF | OFF |
| A5 | L | NONE (THI ON) | OFF | OFF |
| B1 | NONE (SH) | THI OFF OR Filter−THI | OFF | OFF |
| B2 | UH | THI OFF OR Filter−THI | OFF | OFF |
| B3 | H | THI OFF OR Filter−THI | OFF | OFF |
| B4 | M | THI OFF OR Filter−THI | OFF | OFF |
| B5 | L | THI OFF OR Filter−THI | OFF | OFF |

FIG. 12A

| | MENU DESCRIPTION 201 | DENSITY RESTRICTION 202 | THI RESTRICTION 203 | MULTIPLE FOCUSING RESTRICTION 204 | SYNTHETIC APERTURE RESTRICTION 205 |
|---|---|---|---|---|---|
| RESTRICTION DEGREE 0 | OFF | NONE (SH) | NONE (THI ON) | NONE (ON) | NONE (ON) |
| | A1 | NONE (SH) | NONE (THI ON) | OFF | OFF |
| | A2 | UH | NONE (THI ON) | OFF | OFF |
| | A3 | H | NONE (THI ON) | OFF | OFF |
| | A4 | M | NONE (THI ON) | OFF | OFF |
| | A5 | L | NONE (THI ON) | OFF | OFF |
| | B1 | NONE (SH) | THI OFF OR Filter−THI | OFF | OFF |
| | B2 | UH | THI OFF OR Filter−THI | OFF | OFF |
| | B3 | H | THI OFF OR Filter−THI | OFF | OFF |
| | B4 | M | THI OFF OR Filter−THI | OFF | OFF |
| 10 | B5 | L | THI OFF OR Filter−THI | OFF | OFF |

200

ULTRASOUND DIAGNOSTIC APPARATUS, ULTRASOUND DIAGNOSTIC IMAGE GENERATING METHOD, AND PROGRAM

Japanese Patent Application No. 2016-178282 filed on Sep. 13, 2016, including description, claims, drawings, and abstract the entire disclosure is incorporated herein by reference in its entirety.

BACKGROUND

Technological Field

The present invention relates to an ultrasound diagnostic apparatus, an ultrasound diagnostic image generating method, and a program.

Description of the Related Art

With an ultrasound diagnosis, by a simple operation of applying an ultrasound probe on a surface of a testing body, a manner of heartbeat or a movement of a baby in the womb can be obtained with a real-time display, and the test can be repeated thanks to its high safety performance.

An ultrasound diagnostic apparatus creates an image of an inner information of a test object as an ultrasound image based on reflected ultrasound obtained by transmitting and receiving ultrasound to and from the inside of the test object via an ultrasound probe. As the ultrasound images, there is a B-mode image obtained in a B (brightness) mode and a C-mode image obtained in a C (color flow) mode, which is displayed as overlapping on the B-mode image for example.

The B-mode image is an image which is an image of an inner tissue of the test object created by showing an amplitude strength of the reflection ultrasound with brightness.

On the other hand, the C-mode image is an image showing bloodstream information with a color in Region Of Interest (hereinafter, the Region Of Interest is referred to as "ROI") specified in the B-mode image. As the C-mode image, there are a color Doppler image in which the bloodstream information in the ROI is shown by allocating the bloodstream approaching to the ultrasound probe with a red component and the bloodstream flowing away from the ultrasound probe with a blue component for example, and a power Doppler image in which a bloodstream power is shown with a color, and is displayed as overlapping on the B-mode image.

When the C-mode image is displayed, transmission and reception of ultrasound for a B-mode image and transmission and reception of ultrasound for a C-mode image are alternately executed and the generated B-mode image data and C-mode image data are combined and displayed. In this manner, when the C-mode image is displayed, since transmission and reception of ultrasound for a B-mode image and transmission and reception of ultrasound for a C-mode image are needed, transmission and reception take time and the frame rate is lowered, compared to a case of displaying a B-mode image for which only transmission and reception of ultrasound for a B-mode image are needed.

Thus, there is a known ultrasound diagnostic apparatus that can set a different frame rate for each of the frame rate for generating B-mode-image data and the frame rate for generating C-mode-image data, controls a time phase for scanning ultrasound according to the set frame rate, generates a reference signal, and displays the B-mode image data and C-mode image data as overlapping the images based on the reference signal (see JP 2008-142130 A).

In general, in an ultrasound diagnostic apparatus, when a scanning condition such as a scanning density or a depth is determined, a frame rate is determined according to the condition. However, according to the ultrasound diagnostic apparatus of JP 2008-142130 A, since the scanning condition needs to be determined reversely based on the frame rate, the control becomes complicated.

Further, in the ultrasound diagnostic apparatus of JP 2008-142130 A, since the frame rate differs according to the image modes such as a B mode and a C mode, a system to adjust the time phases is needed and the control becomes complicated.

SUMMARY

An object of the present invention is to easily adjust the frame rate of combined image data when combining image data in two different modes.

To achieve the abovementioned object, according to an aspect of the present invention, an ultrasound diagnostic apparatus that can combine image data and has a first image mode and a second image mode, reflecting one aspect of the present invention comprises:

a hardware processor that sets a scan parameter of an image of a first image mode according to restriction information of the scan parameter of the image of the first image mode, which affects a frame rate, when the second image mode is turned on and generates control information corresponding to the set scan parameter;

a transmitter that generates a drive signal according to the generated control information and inputs the drive signal to an ultrasound probe that transmits transmission ultrasound to a test object according to the drive signal and receives reflected ultrasound;

a receiver that generates a reception signal of the images in the first and second image modes from an electric signal generated in the ultrasound probe, according to the generated control information;

a first-image-mode image generator that generates first-image-mode image data based on the generated reception signal of the image of the first image mode;

a second-image-mode image generator that generates second-image-mode image data based on the generated reception signal of the image in the second image mode; and a combiner that generates combined image data by combining the generated first-image-mode image data and the generated second-image-mode image data.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention:

FIG. 3 is a diagram illustrating a configuration of a scan parameter restriction table;

FIG. 12A is a diagram illustrating quantification of restrictions corresponding to a scan parameter restriction table;

DETAILED DESCRIPTION OF EMBODIMENTS

Figure 1:
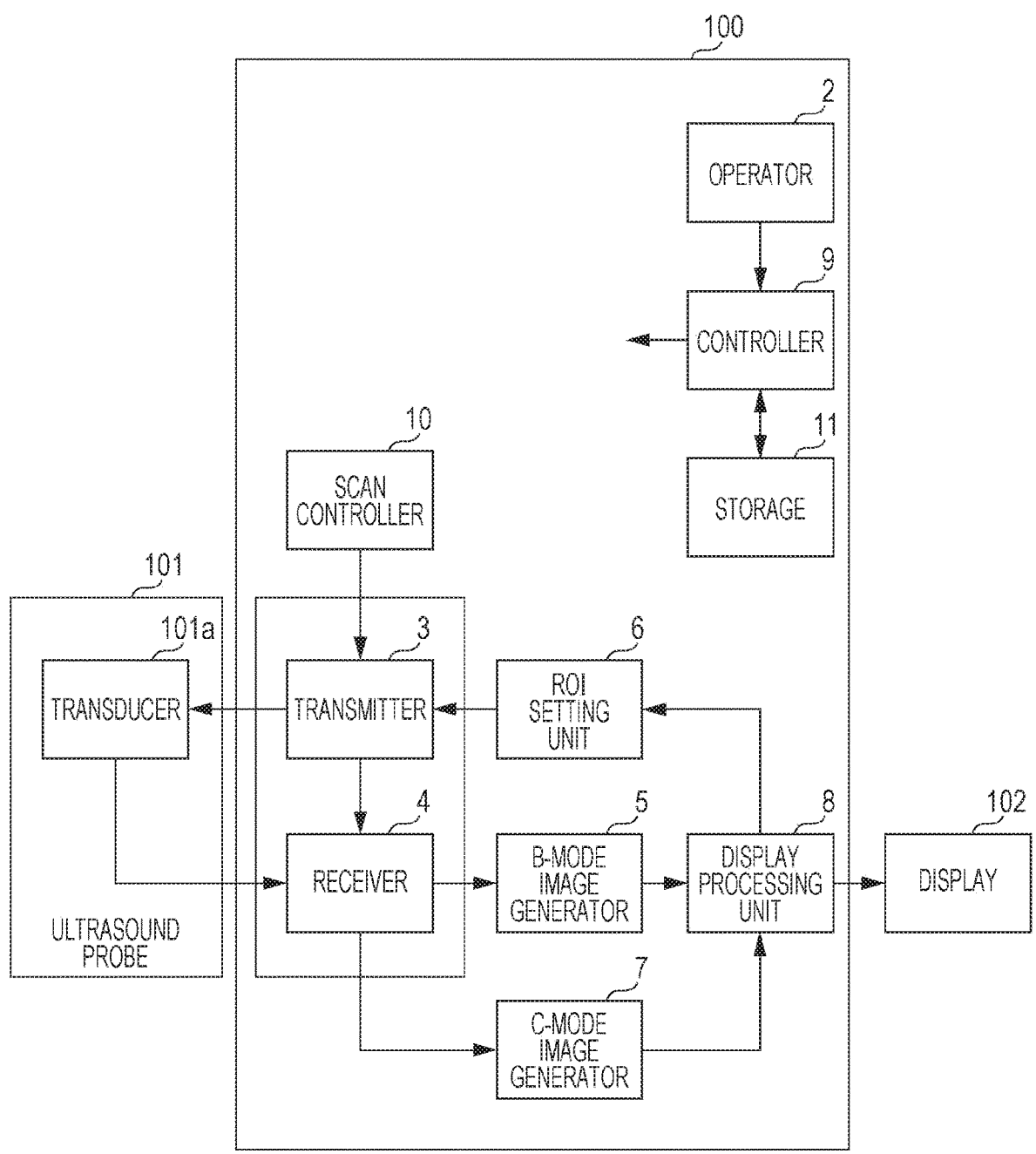
FIG. 1 is a general block diagram illustrating a configuration of an ultrasound diagnostic apparatus according to a first embodiment of the present invention.

Hereinafter, an ultrasound diagnostic apparatus according to first and second embodiments of the present invention will be described with reference to the drawings. However, the scope of the invention is not limited to the disclosed embodiments. Here, in the following description, a component having the same function and configuration will be applied with a same reference numeral and the explanation thereof will be omitted.

First Embodiment

With reference to FIGS. 1 to 10, a first embodiment of the present invention will be described. FIG. 1 is a general block diagram illustrating a configuration of an ultrasound diagnostic apparatus 100 according to the present embodiment. FIG. 1 illustrates that the ultrasound diagnostic apparatus 100 is being connected with an ultrasound probe 101 and a display 102.

The ultrasound diagnostic apparatus 100 includes an operator 2 as first, second third, and fourth operators, a transmitter 3, a receiver 4, a B-mode image generator 5 as a first-image-mode image generator, an ROI setting unit 6, a C-mode image generator 7 as a second-image-mode image generator, a display processing unit 8 as a combiner, a controller 9, a scan controller 10, and a storage 11 as a first and second storages.

The ultrasound probe 101 has a plurality of transducers (voltage conversion elements) 101a which are one-dimensionally arranged, and the transducers 101a respectively convert drive signals (electrical transmission signals) from the transmitter 3 into ultrasound and generate ultrasound beams. Thus, by placing the ultrasound probe 101 on a surface of a test object to be measured, an operator can radiate an ultrasound beam inside the test object. Then, the ultrasound probe 101 receives reflected ultrasound from the inside of the test object, and the plurality of transducers 101a convert the reflected ultrasound into an electrical reception signal and supplies the signals to the later described receiver 4.

Here, the present embodiment describes an example of the ultrasound probe 101 of a linear type in which the plurality of transducers 101a are one-dimensionally arranged; however, this example does not set any limitation. For example, an ultrasound probe 101 of a convex type, a sector type or the like in which the plurality of transducers 101a are one-dimensionally arranged, an ultrasound probe 101 in which the plurality of transducers 101a are two-dimensionally arranged, an ultrasound probe 101 in which one-dimensionally arranged plurality of transducers 101a vibrate, or the like may be used. Further, based on a control by the scan controller 10 (the controller 9), the transmitter 3 selects a transducer 101a used by the ultrasound probe 101, and controls a radiating position or a radiating direction of an ultrasound beam that the ultrasound probe 101 transmits by respectively changing timing of giving voltage to the transducer 101a or a value of the voltage.

Further, the ultrasound probe 101 may include a part of functions of the later described transmitter 3 and receiver 4. For example, the ultrasound probe 101 may have a configuration for generating a drive signal in the ultrasound probe 101 based on a control signal (hereinafter, referred to as a "transmission control signal") used to generate a drive signal output from the transmitter 3, converting the drive signal into ultrasound by the transducer 101a, converting the received reflected ultrasound into an electrical reception signal, and generating a later described reception signal based on the electrical reception signal in the ultrasound probe 101.

Further, the ultrasound probe 101 is electrically connected to the ultrasound diagnostic apparatus 100 via a cable in general; however, this does not set any limitation and, for example, the ultrasound probe 101 may have a configuration to wirelessly transmit and receive a transmission signal and a reception signal to and from the ultrasound diagnostic apparatus 100. Here, in a case of such a configuration, it is obvious that the ultrasound diagnostic apparatus 100 and ultrasound probe 101 include a communication unit that can perform a wireless communication.

The display 102 is a so-called monitor, which displays image data output from the ultrasound diagnostic apparatus 100 (the display processing unit 8). Here, the present embodiment describes a configuration in which the display 102 is connected to the ultrasound diagnostic apparatus 100; however, for example, in a case of a touch panel type ultrasound diagnostic apparatus, in which the display 102 and the later described operator 2 are integrally provided and the operator 2 is operated by touching the display 102, the ultrasound diagnostic apparatus 100 and display 102 are integrally provided. Here, the present embodiment describes that "the display 102 is connected to the ultrasound diagnostic apparatus 100" even in a case that the ultrasound diagnostic apparatus 100 and the display 102 are integrally provided.

The operator 2 receives an input by an operator and outputs an instruction based on the operator's input to the ultrasound diagnostic apparatus 100, that is more specifically, the controller 9. The operator 2 has a function that allows the operator to select a mode to display a B-mode image only (hereinafter, referred to as a "B mode") or a mode to display a C-mode (color flow mode) image overlapping on the B-mode image (hereinafter, referred to as a "C mode"). Then, the operator 2 also includes a function that allows the operator to specify a position of ROI where the C-mode image is displayed on the B-mode image. Further, as a C-mode image to be displayed, there are C-mode images of display modes including a V mode for displaying a current speed and direction of a bloodstream with a color based on a bloodstream velocity V as a bloodstream signal indicting a condition of the bloodstream, a P mode for displaying a bloodstream power with a color based on a power P of the bloodstream as a bloodstream signal, and a V-T mode for displaying the current speed and a turbulence of the bloodstream based on the bloodstream velocity V and a turbulence T as a bloodstream signal. When an input in the C mode is accepted from the operator, the operator 2 is assumed to also accept its display mode. Here, the display mode of the C-mode image may include a T (turbulence) mode, a dP (directional power) mode, and the like. In this manner, the C mode includes a color Doppler mode (V mode, V-T mode, etc.) and a power Doppler mode (P mode, etc.).

The transmitter 3 generates at least a drive signal, and performs a transmission process for transmitting an ultrasound beam to ultrasound probe 101. As an example, the transmitter 3 performs a transmission process for generating a transmission signal to transmit an ultrasound beam from the ultrasound probe 101 having the transducer 101a and drives the transducer 101a of the ultrasound probe 101 by supplying a high-voltage electrical transmission signal, which occurs at a predetermined timing, to the ultrasound probe 101 based on the transmission signal. With this configuration, the ultrasound probe 101 can emit the ultrasound beam to the test object, which is a subject to be measured, by converting the electrical transmission signal into ultrasound.

When the C mode is turned on, the transmitter 3 performs a transmission process to display a C-mode image according to a control by the scan controller 10, in addition to a transmission process to display a B-mode image. For example, after supplying an electrical transmission signal for displaying the B-mode image, repeated supplies of a drive signal for QSP (quad signal processing) to display the C-mode image in a same direction (the same line) for n times (n is 6 to 12 for example) are performed for all direction (all lines) of the ROI set by the ROI setting unit 6. It is noted that the present embodiment is not limited to the drive signal for the QSP. Further, the transmitter 3 specifies additional information of the B-mode image transmission process or the C-mode image transmission process during the transmission process and supplies the additional information to the receiver 4.

Further, when generating a B-mode image according to the control by the scan controller 10, the transmitter 3 performs a transmission process for generating a B-mode image according to a scan parameter set by the scan controller 10. In the B mode or C mode, the scan parameter is assumed to be a parameter related to scanning of the B mode image data to be generated. According to the present embodiment, based on the control by the controller 9, the scan controller 10 controls the process related to the scanning by the transmitter 3 and receiver 4 by restricting a scan parameter that affects the frame rate among the scan parameters related to the image qualities of the B mode image data to be generated, according to need. The scan parameter affecting the frame rate controlled by the scan controller 10 is assumed to be a scan density, a THI of a pulse inversion method, multiple focusing, and a synthetic aperture as described later.

According to the control by the controller 9, the receiver 4 performs a reception process for generating a reception signal as an electronic radio frequency (RF) signal based on the reflected ultrasound. The receiver 4 generates a reception signal (sound ray data) by receiving the reflected ultrasound with the ultrasound probe 101 for example, and performing an A/D conversion and phase summing on the electrical reception signal, which is converted based on the reflected ultrasound, as amplifying the electrical reception signal.

The receiver 4 acquires additional information from the transmitter 3, supplies the reception signal to the B-mode image generator 5 when the acquired additional information is additional information of a B-mode image, and supplies the reception signal to the C-mode image generator 7 when the acquired additional information is additional information of C-mode image. Hereinafter, a reception signal used to generate a B-mode image is referred to as a "B mode reception signal," and a reception signal used to generate a C-mode image is referred to as a "C mode reception signal."

Here, the present embodiment describes a configuration that the receiver 4 sorts the reception signals related to a generated image frame into a signal for a B-mode image and a signal for a C-mode image and supplies the signals to each block; however, this example does not set any limitation and, for example, there may be a configuration that the B-mode image generator 5 and C-mode image generator 7 respectively sort the reception signals related to a generated image frame.

According to the control by the controller 9, the B-mode image generator 5 executes an envelope detection, a logarithmic compression, or the like on the B-mode reception signal input by the receiver 4 and performs a brightness conversion by adjusting a dynamic range or a gain to generate a B-mode image data and output the B mode image data to the display processing unit 8. Especially, the B-mode image generator 5 generates a B-mode image data according to the scan parameter set by the controller 9.

Figure 2:
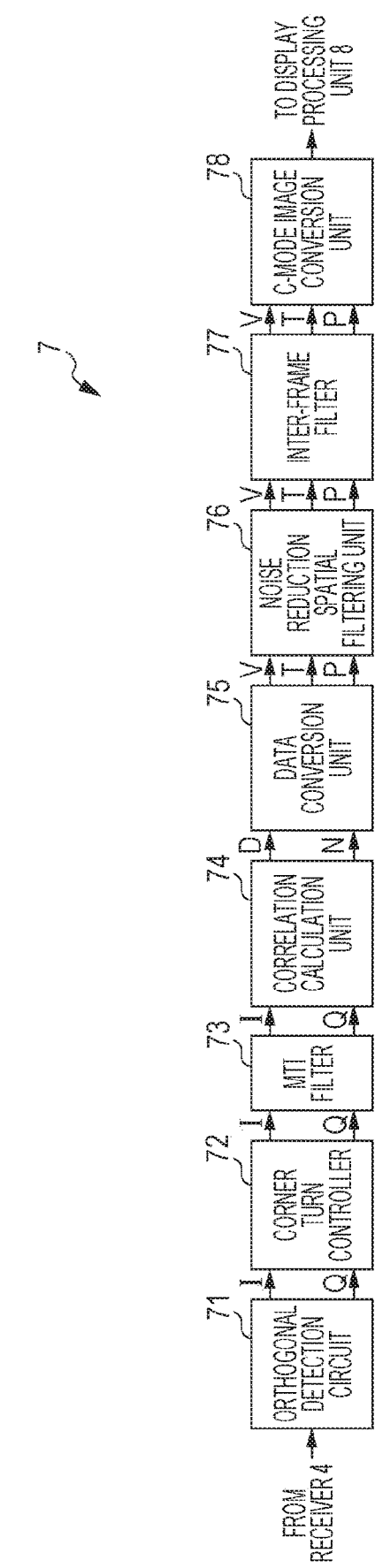
FIG. 2 is a block diagram illustrating an internal configuration of a C-mode image generator.

According to the control by the controller 9, the C-mode image generator 7 generates a C-mode image data and outputs the C mode image data to the display processing unit 8 according to the C-mode reception signal input by the receiver 4. Here, with reference to FIG. 2, an internal configuration of the C-mode image generator 7 will be described. FIG. 2 is a block diagram illustrating an internal configuration of the C-mode image generator 7. As illustrated in FIG. 2, the C-mode image generator 7 includes an orthogonal detection circuit 71, a corner-turn controller 72, a moving target indication (MTI) filter 73, a correlation calculation unit 74, a data conversion unit 75, a noise reduction spatial filtering unit 76, an inter-frame filter 77, and a C-mode image conversion unit 78.

According to the control by the controller 9, the orthogonal detection circuit 71 performs an orthogonal detection on a C-mode reception signal input by the receiver 4 to calculate a phase difference between the acquired C-mode reception signal and a reference signal, and acquires complex Doppler signals I and Q.

According to the control by the controller 9, the corner-turn controller 72 stores, in a memory (not illustrated), the Doppler signals I and Q input from the orthogonal detection circuit 71 as arranging for each same acoustic line in a depth direction from the ultrasound probe 101 to the test object and in an ensemble direction of a repetition number n of ultrasound transmissions and receptions and reads the Doppler signals I and Q in the ensemble direction for each depth.

The reception signal (the Doppler signals I and Q) includes information (a clutter component) of an unnecessary blood vessel wall, a tissue, or the like in addition to a signal component of a bloodstream needed to generate a C-mode image. According to the control by the controller 9, the MTI filter 73 filters the Doppler signals I and Q output from the corner-turn controller 72 and removes clutter components.

According to the control by the controller 9, the correlation calculation unit 74 calculates a real part D and an imaginary part N of an average value S of autocorrelation calculation of Doppler signal (an average value of phase difference vectors) from the Doppler signals I and Q (complex Doppler signal z) which are filtered by the MTI filter 73.

[Expression 1]

$$S = \sum_{k=1}^{n-1} \overline{z_k} \cdot z_{k+1} = D + jN \quad (1)$$

According to the control by the controller 9, the data conversion unit 75 calculates a bloodstream velocity V, a power P, and a turbulence T based on the Doppler signals I and Q filtered by the MTI filter 73, the real part D and imaginary part N of the average value S of the Doppler signal autocorrelation calculation. More specifically, by using following Expression 2, the data conversion unit 75 calculates the bloodstream velocity V based on the real part D and imaginary part N of the average value S of the Doppler signal autocorrelation calculation.

[Expression 2]

$$V = \tan^{-1} \frac{N}{D} \quad (2)$$

Further, by using following Expression 3, the data conversion unit 75 calculates the power P as a strength average value of the Doppler signals based on the Doppler signals I and Q (the complex Doppler signal z).

[Expression 3]

$$P = \frac{1}{n} \sum_{k=1}^{n} |z_k|^2 \quad (3)$$

Further, by using following Expression 4, the data conversion unit 75 calculates the turbulence T as a ratio between sizes and powers of the phase difference vectors (Here, the ratio is extracted from one and then the magnitude relation is reversed.) based on the Doppler signals I and Q (the complex Doppler signal z).

[Expression 4]

$$T = 1 - \frac{\sqrt{D^2 + N^2}}{P} \quad (4)$$

The noise reduction spatial filtering unit 76 filters the power P calculated by the data conversion unit 75, the bloodstream velocity V, and the turbulence T. The noise reduction spatial filtering unit 76 includes a keyhole filter and a spatial filter (None of them is illustrated).

The keyhole filter filters the power P, bloodstream velocity V, and turbulence T which compose the frame of a C-mode image and removes noise. In the V mode and V-T mode, the keyhole filter removes the bloodstream velocity V in a set removal region by using the bloodstream velocity V and power P calculated by the data conversion unit 75 and filters the bloodstream velocity V. In the V mode and V-T mode, the bloodstream velocity V is used to display (color) an image. In the P mode, the keyhole filter removes the power P in a set removal region by using the bloodstream velocity V and power P calculated by the data conversion unit 75 and filters the power P. In the P mode, the power P is used to display (color) an image.

More specifically, in the V mode and V-T mode, the keyhole filter removes a bloodstream velocity V as assuming a bloodstream signal in a region where the bloodstream velocity V is smaller than a predetermined threshold value as a clutter noise and assuming a bloodstream signal in a region where the power P is smaller than the predetermined threshold value as a background noise. Further, in the P mode, the keyhole filter removes a power P in a region as assuming that the bloodstream signal in the region where the bloodstream velocity V is smaller than the predetermined threshold value as a clutter nose and assuming that the bloodstream signal in the region where the power P is smaller than the predetermined threshold value as a background noise.

The spatial filter is a two-dimensional weighted average filter to smooth data of the bloodstream velocity V, power P, and turbulence T that compose the frame of the C-mode image. In the V mode or V-T mode, the spatial filter filters the bloodstream velocity V filtered by the keyhole filter and a turbulence T calculated by the data conversion unit 75. In the P mode, the spatial filter filters the power P filtered by the keyhole filter.

The inter-frame filter 77 filters a bloodstream component in each frame that composes the C-mode image according to the display mode input by operating the operator 2, among the bloodstream velocity V, power P, and turbulence T filtered by the noise reduction spatial filtering unit 76, so as to smooth the changes between the frames and keep an image lag.

The C-mode image conversion unit 78 generates C-mode image data by converting the bloodstream velocity V, power P, and turbulence T which are filtered by the inter-frame filter 77.

The display processing unit 8 performs a process to form image display data to be displayed on the display 102 and display the image data on the display 102. Specifically, when the B mode is being selected, the display processing unit 8 performs a process to include the B-mode image of the B-mode image data generated by the B-mode image generator 5 in the display image data as an ultrasound image. Further, when the C mode is being selected, the display processing unit 8 performs a process to generate combined image data, as an ultrasound image, in which the C-mode image of the C-mode image data generated by the C-mode image generator 7 is overlapped in a position of a selected ROI on the B-mode image generated by the B-mode image generator 5, and include the combined image to the display image data.

The controller 9 is composed of a central processing unit (CPU), a read only memory (ROM), and a random access memory (RAM) for example, reads various processing programs such as a system program stored in the ROM, develops the program in the RAM, and controls operations of each unit in the ultrasound diagnostic apparatus 100 according to the developed program. The RAM forms a work area to temporarily store the various programs, which are executed by the CPU, and data related to the programs. The ROM is composed of a non-volatile memory such as a semiconductor for example, and stores the system program for the ultrasound diagnostic apparatus 100, an initial setting program executable in the system program, various processing programs such as an ultrasound diagnosis program, various data, and the like. These programs are stored in a format of a computer readable program code, and the CPU sequentially executes operation according to the program code. Especially, in the ROM, it is assumed that a first ultrasound diagnosis program, a first scan parameter restriction change program, and a scan parameter setting change program are stored.

The storage 11 is composed of a large capacity recording medium such as a hard disk drive (HDD) for example and stores a later described scan parameter restriction table 200, ultrasound image data (B-mode image data and C-mode image data) and the like.

Figure 4:
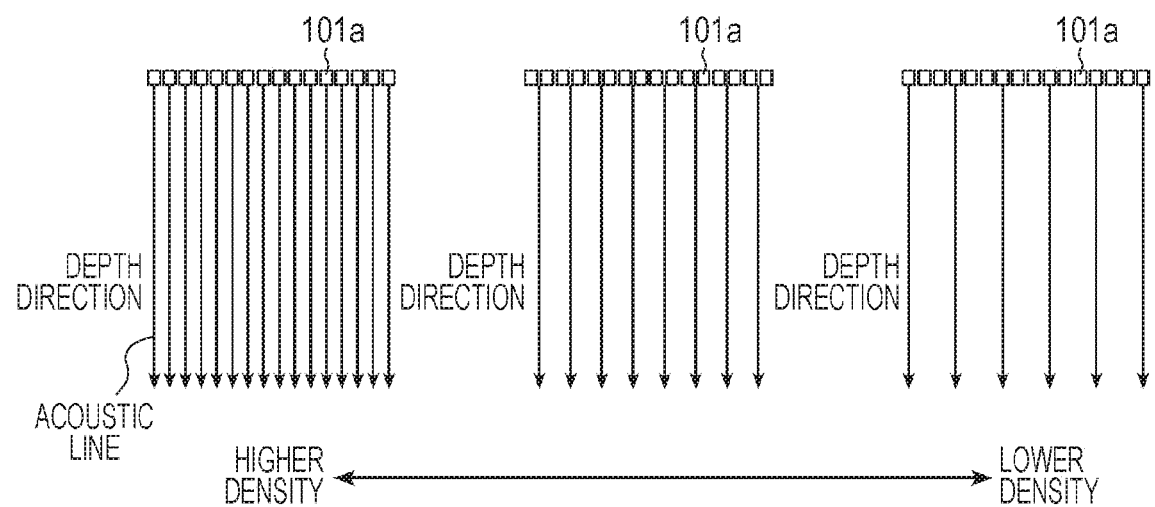
FIG. 4 is a diagram for explaining a scan density.
Figure 5:
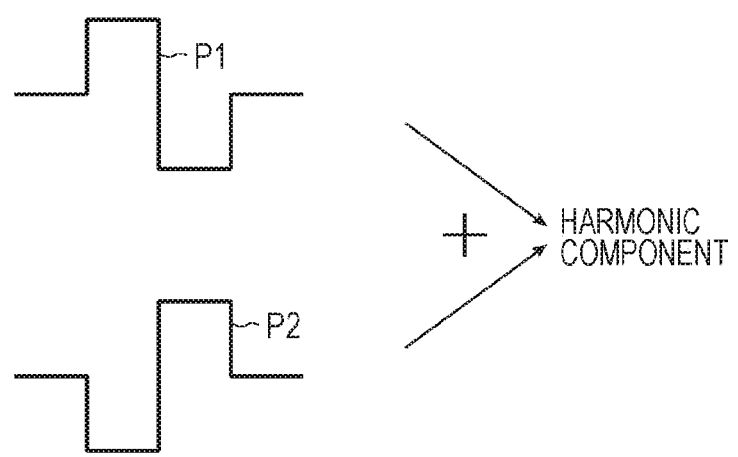
FIG. 5 is a diagram for explaining Tissue Harmonic Imaging (THI) of a pulse inversion method.
Figure 6:
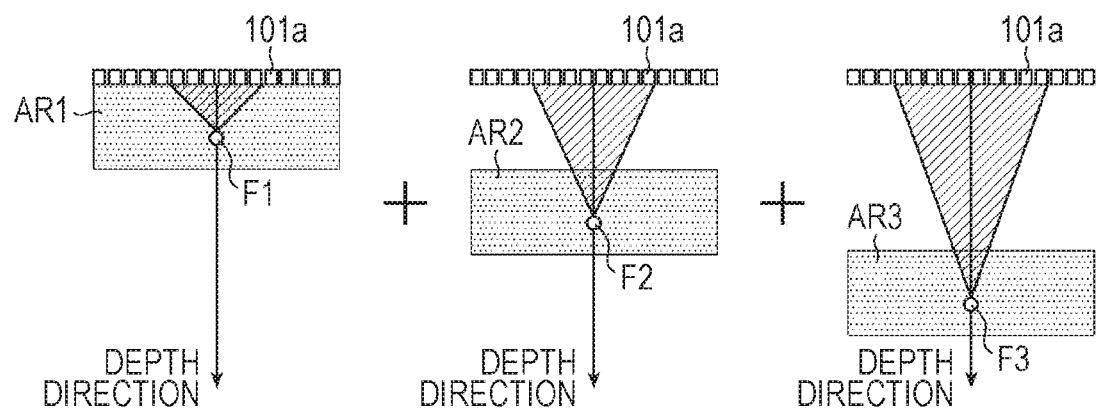
FIG. 6 is a diagram for explaining multiple focusing.
Figure 7:
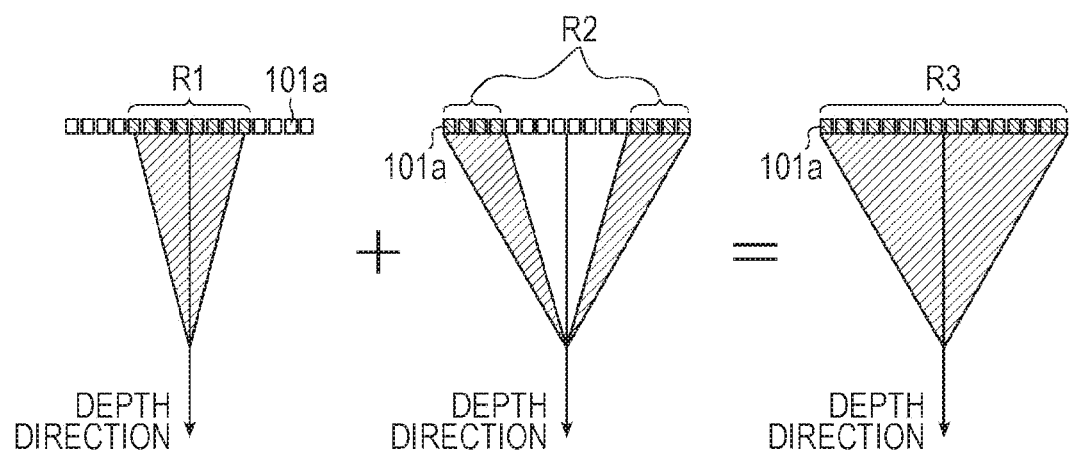
FIG. 7 is a diagram for explaining a synthetic aperture.

Here, with reference to FIGS. 3 to 7, the scan parameter restriction table 200 stored in the storage 11 will be described. FIG. 3 is a diagram illustrating a configuration of the scan parameter restriction table 200. FIG. 4 is a diagram for explaining a scan density. FIG. 5 is a diagram for explaining a THI of a pulse inversion method. FIG. 6 is a diagram for explaining multiple focusing. FIG. 7 is a diagram for explaining a synthetic aperture.

The scan parameter restriction table 200 is a table, regarding various parameters for scanning a B-mode image (hereinafter, referred to as scan parameters), including restriction information of scan parameters affecting frame rates, which are respectively set for each menu descriptions. The scan parameter restriction table 200 has items of a menu description 201, a density restriction 202, a tissue harmonic imaging (THI) restriction 203, a multiple focusing restriction 204, and a synthetic aperture restriction 205.

The menu description 201 is a description of a menu of restrictions of the scan parameters which can be selected and input by an operator. As the menu description 201, there are "Off" indicating that there is no restriction related to the scan parameter, "A1" to "A5" indicating that there is no restriction related to the THI restriction 203, and "B1" to "B5" indicating that there is a restriction related to the THI restriction 203.

The density restriction 202 is restriction information related to a scan density as the scan parameter corresponding to the menu description 201. Here, with reference to FIG. 4, the scan density will be described. As illustrated in FIG. 4, the scan density is a density of an acoustic line of the plurality of transducers 101a of the ultrasound probe 101. A higher density causes a better image quality; however, the frame rate becomes lowered since transmissions and receptions need to be performed with a large number of acoustic lines.

The density restriction 202 is restriction information as an upper limit value of settable scan densities, and there are Non (SH: super high), UH (ultra high), H (high), M (middle), and L (low) in order of lower restrictions.

The THI restriction 203 is restriction information of THI of a pulse inversion method as the scan parameter corresponding to the menu description 201. Here, with reference to FIG. 5, THI of the pulse inversion method will be described. The pulse inversion method is a method to output a drive signal twice in waveforms in which positive and negative are inverted from the transmitter 3 to the ultrasound probe 101 and adds the reception signals acquired by the receiver 4 to cancel a fundamental wave component and obtain a harmonic component. For example, as illustrated in FIG. 5, the drive signal P1 and the drive signal P2 in which the positive and negative of the drive signal P1 are inverted are sequentially generated. In the THI of the pulse inversion method (imaging using a harmonic component), since two-time ultrasound transmissions and receptions are needed for each acoustic line, the frame rate becomes a half compared to a case that the THI of the pulse inversion method is not used and one-time transmission and reception is needed per acoustic line. As the THI, in addition to the THI of the pulse inversion method, there is a Filter-THI for imaging by filtering signals other than a harmonic component of the reception signal and obtaining the harmonic component, and, in this method, only one-time ultrasound transmission and reception is needed per acoustic line.

The THI restriction 203 is restriction information indicating whether or not to restrict the THI execution of the pulse inversion method and there are Non (the THI of the pulse inversion method is on) and THI off or Filter-THI (on) (of the pulse inversion method) in order of lower restrictions.

The multiple focusing restriction 204 is restriction information of multiple focusing as a scan parameter corresponding to the menu description 201. Here, with reference to FIG. 6, multiple focusing will be described. The multiple focusing is a method to perform multiple-time transmissions and receptions of ultrasound as changing a transmission focus depth and generate a reception signal of one acoustic line as combining the reception signals acquired by transmitting and receiving more than one time. In the multiple focusing, since more than one ultrasound transmissions and receptions are needed for each acoustic line, the frame rate becomes lower compared to a case that the multiple focusing is not used.

As illustrated in FIG. 6, ultrasound is transmitted by a transmission focus F1 of a small focus depth for the first time to acquire a reception signal in a small reception depth range AR1, ultrasound is transmitted by a transmission focus F2 of a medium focus depth for the second time to receive a reception signal in a medium reception depth range AR2, ultrasound is transmitted by a transmission focus F3 of a large focus depth for the third time to acquire a reception signal in a large reception depth range AR3, so that the reception signals in a wide reception depth range are acquired from the reception signals of the three-time transmissions and receptions. FIG. 6 is an example in which the steps of the multiple focusing is three; however, the process will be the same in a case with different number of steps.

The multiple focusing restriction 204 is restriction information indicating whether or not to restrict multiple focusing execution, and there are Non (multiple focusing is on) and Off (multiple focusing is off) in order of lower restrictions.

The synthetic aperture restriction 205 is restriction information of the synthetic aperture as a scan parameter corresponding to the menu description 201. Here, with reference to FIG. 7, the synthetic aperture will be described. The synthetic aperture is a method for selecting a reception aperture of the plurality of transducers 101a among all the transducers 101a of the ultrasound probe 101, combining the reception signals of two-time ultrasound transmissions and receptions, and acquiring an effect of a reception with a large aperture. This is because that the upper limit value of the number of the transducer 101a (channels) which can be used as a reception aperture has been determined. Here, since a large aperture is realized by the two-time ultrasound transmissions and receptions, the frame rate becomes a half.

As illustrated in FIG. 7, the first ultrasound reception is performed by an inner reception aperture R1, the second ultrasound reception is performed by an outer reception aperture R2, and the reception signals of the reception apertures R1 and R2 are combined, a reception signal, which looks like a signal received by a reception aperture R3 of a large aperture, can be obtained.

The synthetic aperture restriction 205 is restriction information indicating whether or not to restrict a synthetic aperture execution, and there are None (synthetic aperture is on) and Off (synthetic aperture is off) in order of lower restrictions.

Figure 8:
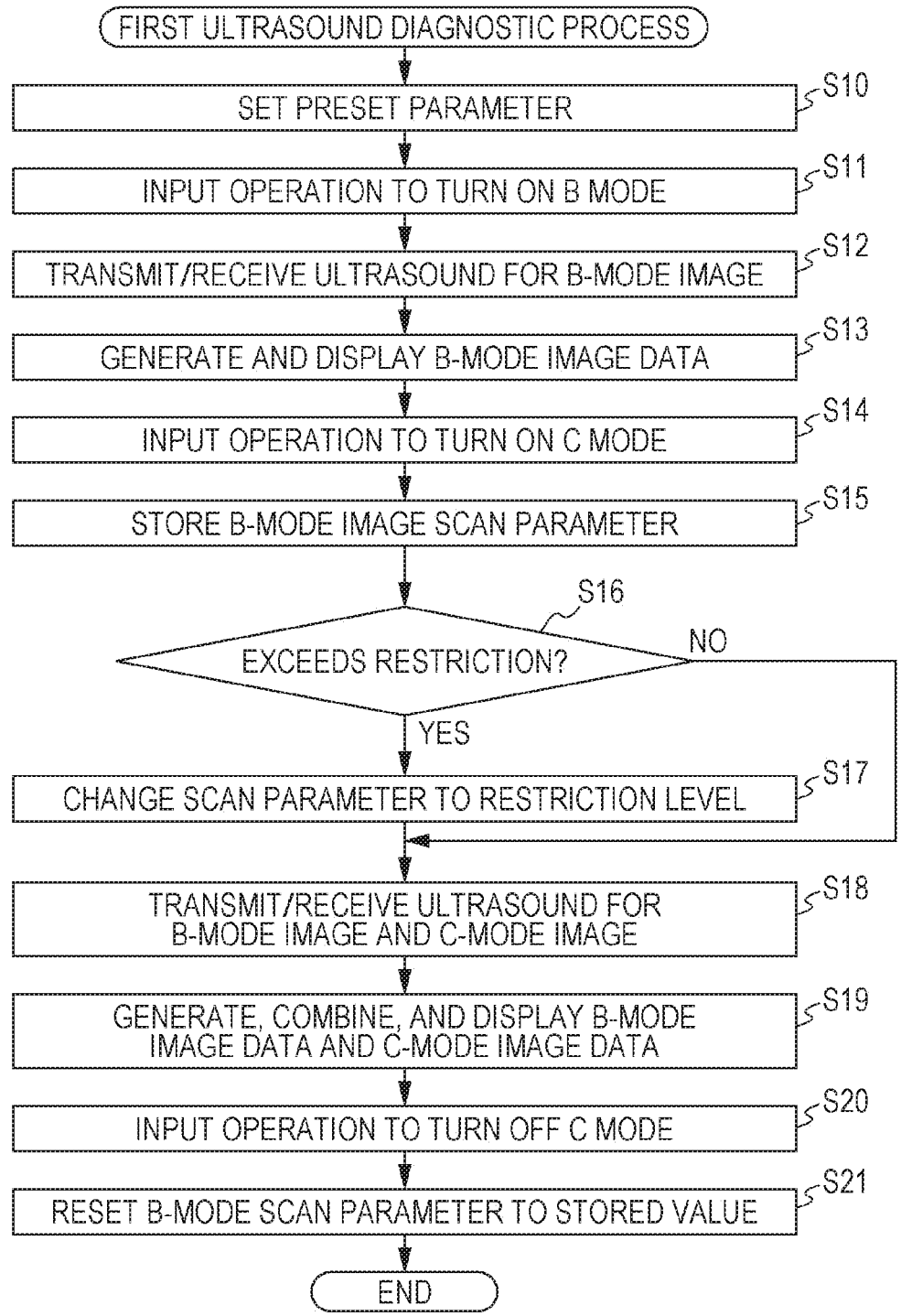
FIG. 8 is a flowchart illustrating a first ultrasound diagnostic process.
Figure 9A:
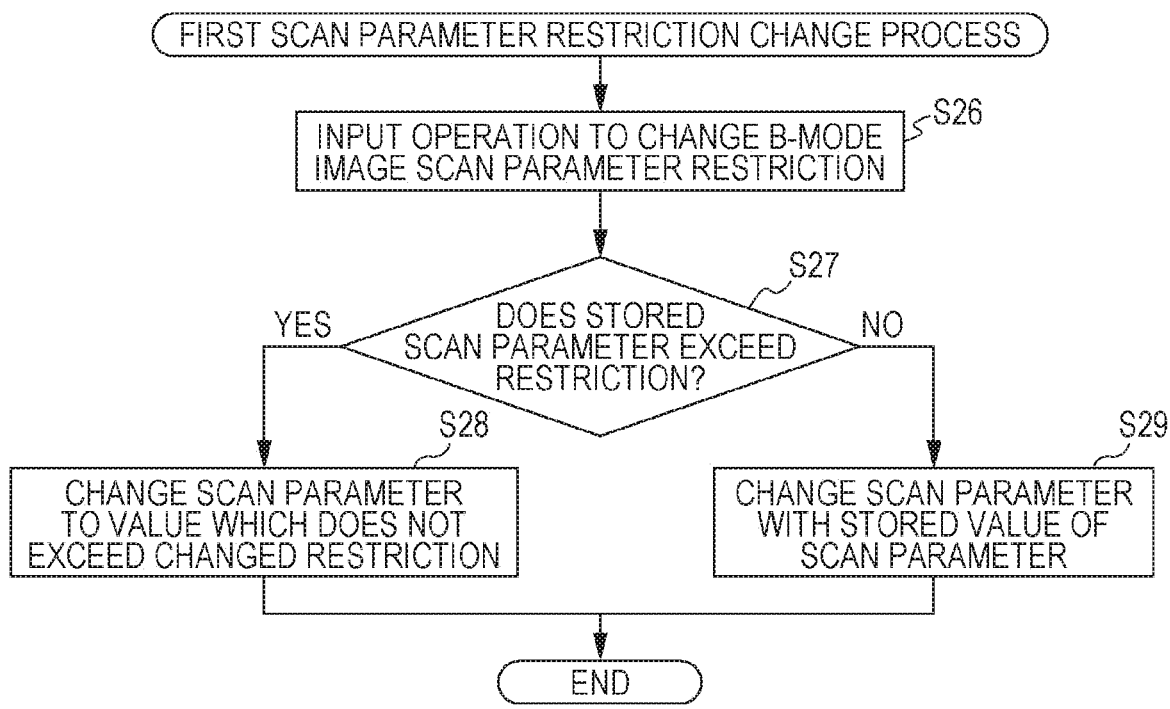
FIG. 9A is a flowchart illustrating a first scan parameter restriction change process.
Figure 9B:
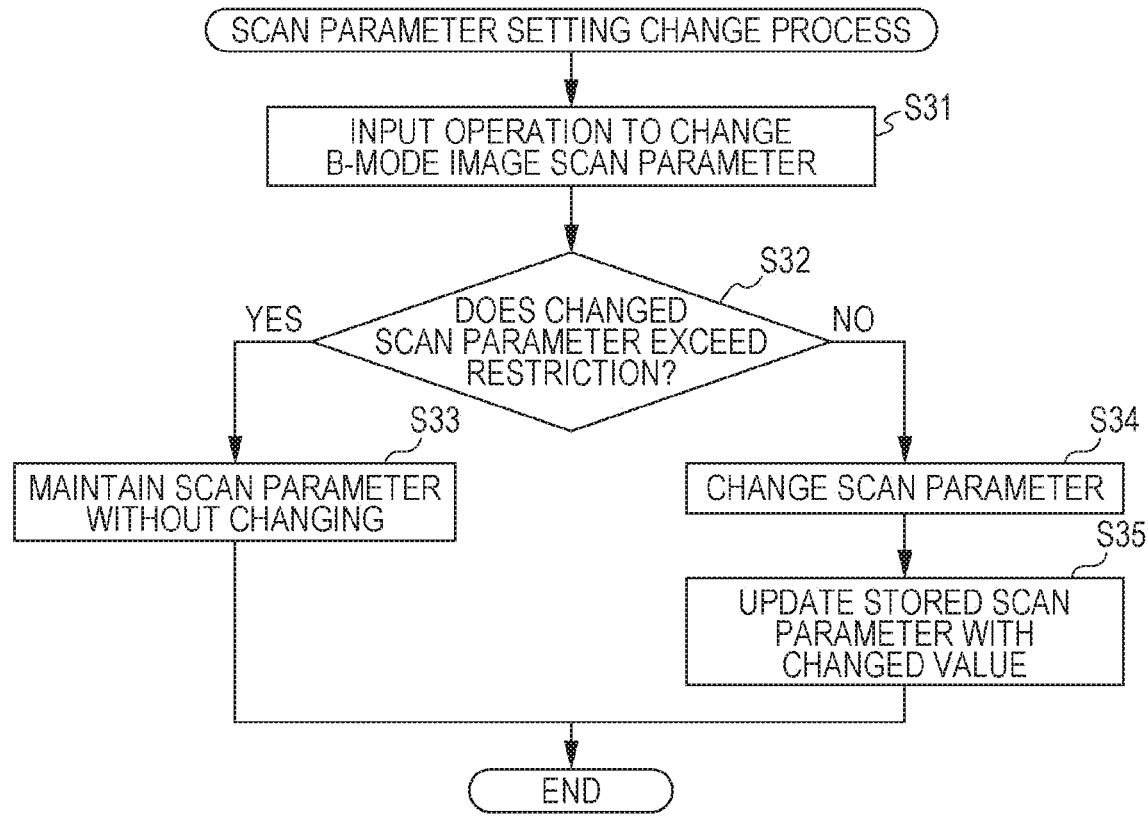
FIG. 9B is a flowchart illustrating a scan parameter setting change process.
Figure 10:
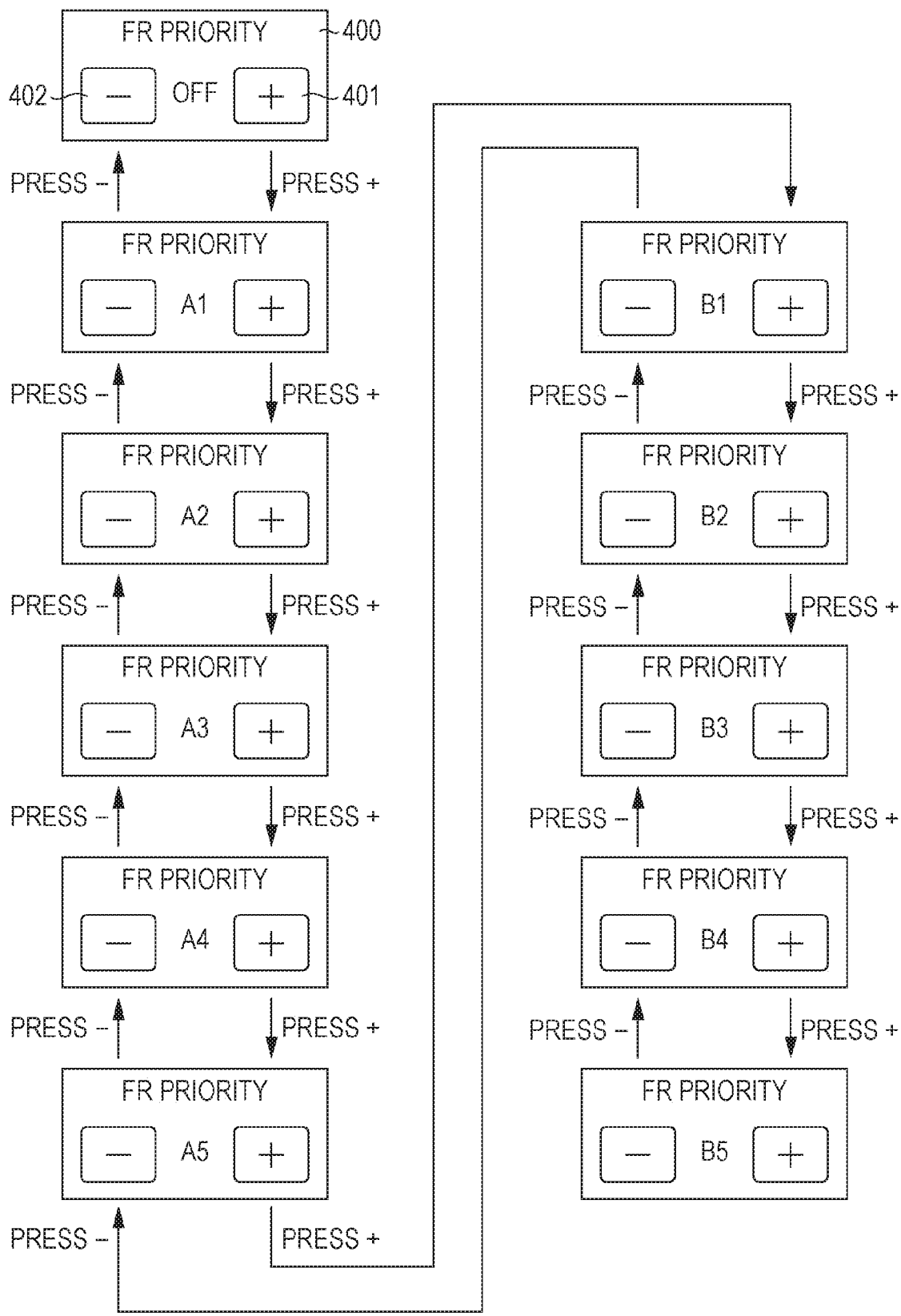
FIG. 10 is a diagram illustrating a transition of a scan parameter restriction menu region.

Next, with reference to FIGS. 8 to 10, operations of the ultrasound diagnostic apparatus 100 will be described. FIG. 8 is a flowchart illustrating a first ultrasound diagnostic process. FIG. 9A is a flowchart illustrating a first scan parameter restriction change process. FIG. 9B is a flowchart illustrating a scan parameter setting change process. FIG. 10 is a diagram illustrating a transition of a scan parameter restriction menu region 400.

Firstly, with reference to FIG. 8, the first ultrasound diagnostic process executed by the ultrasound diagnostic apparatus 100 will be described. The first ultrasound diagnostic process is an example of the ultrasound diagnostic process and is a process for generating and displaying ultrasound image data of the test object in each mode after a transition from the B mode, the C mode, and to the B mode. In the ultrasound diagnostic apparatus 100, for example, in response to an instruction of executing the first ultrasound diagnostic process input by an operator (a technologist, a doctor, or the like) via an operator 2, the controller 9 executes the first ultrasound diagnostic process according to the first ultrasound diagnosis program stored in the ROM.

As illustrated in FIG. 8, firstly, the controller 9 sets a preset parameter, which is set according to a diagnosed part of the test object. The preset parameter includes a B-mode image scan parameter (the scan density, THI of the pulse inversion method, multiple focusing, and synthetic aperture) and a restriction of the B-mode image scan parameter (step S10).

Then, the controller 9 accepts an input of an operation to turn on the B mode by the operator via the operator 2 (step S11). When the B mode is turned on, the controller 9 accepts an input of various setting information of the B-mode image scan parameter (the scan density, THI of the pulse inversion method, multiple focusing, synthetic aperture) according to need. In the B mode and C mode, the operator applies the ultrasound probe 101 onto the test object according to need.

Further, the controller 9 can accept an input of selecting a menu of scan parameter restriction from the operator via the operator 2 according to need. More specifically, the controller 9 performs control to display, on the display processing unit 8, the scan parameter restriction menu region 400 illustrated in FIG. 10 on the screen of the display 102. The scan parameter restriction menu region 400 has a + button 401 and a − button 402. In response to a touch input on the + button 401 or − button 402 via the operator 2, the menu description is switched between Off, A1 to A5, and B1 to B5, and one of the menu description is selected.

Then, according to the setting information of the preset B-mode image scan parameter or setting information of the input B-mode image scan parameter, the controller 9 controls, via the scan controller 10, the transmitter 3 to generate a drive signal for a B-mode image, the ultrasound probe 101 to transmit ultrasound, the receiver 4 to generate a B-mode reception signal according to the reflected ultrasound input to the ultrasound probe 101, so as to transmit and receive the ultrasound for the B-mode image (step S12).

Then, the controller 9 controls the B-mode image generator 5 to generate B-mode image data based on the reception signal generated in step S12 and the display processing unit 8 to display the generated B-mode image data on the display 102 (step S13). Then, the controller 9 accepts, from the operator, an input of an operation to turn on the C mode via the operator 2 (step S14).

Here, it is assumed that, when the C mode is on, the controller 9 accepts, from the operator, an input to change the restriction information of the scan parameter according to need by executing the later described first scan parameter restriction change process. Further, it is assumed that, by executing the later described scan parameter setting change process, the controller 9 accepts an input to change the setting information of the scan parameter from the operator according to need.

Then, the controller 9 stores, to the storage 11, latest setting information of the scan parameter which is input while the B mode is on in steps S11 to S13 (step S15). Then, the controller 9 refers to the scan parameter restriction table 200 stored in the storage 11 and determines whether or not the setting information of the current scan parameter in the B-mode image is greater than any of the restriction items 202, 203, 204, and 205 of the menu description 201, which is being selected and set, in the scan parameter restriction table 200 (step S16). The setting information of the current scan parameter is setting information of the scan parameter stored in the storage 11 or setting information of the scan parameter changed by the later described scan parameter setting change process.

When the current setting information is greater than the restriction items 202, 203, 204, and 205 of the menu description 201 which is being selected and set (step S16, YES), the controller 9 changes the level of the setting information of the current scan parameter, which is greater than the restriction item, to a restriction level of the restriction items 202, 203, 204, and 205 of the menu description 201 which is being selected and set (step S17).

Then, the controller 9 repeats a B-mode-image ultrasound transmission/reception in which the controller 9 controls, via the scan controller 10, the transmitter 3 to generate a drive signal for the B-mode image according to the setting information of the current scan parameter in the B-mode image, the ultrasound probe 101 to transmit ultrasound, and the receiver 4 to generate a B-mode reception signal corresponding to reflected ultrasound input to the ultrasound probe 101 and a C-mode-image ultrasound transmission/reception in which the controller 9 controls the transmitter 3 to generate a drive signal for a C-mode image according to an ROI set by the ROI setting unit 6, the ultrasound probe 101 to transmit ultrasound, and the receiver 4 to generate a C-mode reception signal according to reflected ultrasound input to the ultrasound probe 101 (step S18). When the current setting information is not greater than any of the restriction items 202, 203, 204, and 205 of the menu description 201 which is being selected and set (NO in step S16), the process proceeds to step S18.

Then, the controller 9 controls the B-mode image generator 5 to generate B-mode image data from the reception signal for the B-mode image generated in step S18, the C-mode image generator 7 to generate C-mode image data of ROI from the reception signal for the C-mode image generated in step S18, the display processing unit 8 to generate combined image data by combining the generated C-mode image data of ROI with the generated B-mode image data, and the display 102 to display the data (step S19).

Then, the controller 9 accepts an input of an operation to turn off the C mode by the operator via the operator 2 (step S20). Then, the controller 9 resets the current scan parameter setting information of the B-mode image in the B mode to the scan parameter setting information stored in the storage 11 (step S21) and ends the first ultrasound diagnostic process. After step S21, for example, similarly to steps S12 and S13, the B-mode image data is generated and displayed.

Next, with reference to FIG. 9A, the first scan parameter restriction change process executed by the ultrasound diagnostic apparatus 100 will be described. The first scan parameter restriction change process is a process to manually change the scan parameter restriction information of a B-mode image when the C mode is on. In the ultrasound diagnostic apparatus 100, for example, the C mode is turned on in step S14 of the first ultrasound diagnostic process, the controller 9 executes the first scan parameter restriction change process according to the first scan parameter restriction change program stored in the ROM, in response to a start of an input of an operation to change the restriction information of the scan parameter setting information of the B-mode image by the operator via the operator 2. The input of an operation to change the restriction information of the B-mode image scan parameter is performed by a touch input on the + button 401 and − button 402 of the scan parameter restriction menu region 400 in FIG. 10, which is displayed on the display 102 as described above for example.

As illustrated in FIG. 9A, firstly, the controller 9 finishes accepting an input of an operation to change the restriction information of the B-mode image scan parameter from the operator via the operator 2 (step S26). Then, the controller 9 refers to the scan parameter restriction table 200 stored in the storage 11 and determines whether or not the setting information of the scan parameter stored in the storage 11 in a case that C mode is on is greater than the restriction items 202, 203, 204, and 205 of the menu description 201 of the restriction information or the scan parameter changed in step S26 (step S27).

When the setting information is greater than at least one of the restriction items 202, 203, 204, and 205 of the menu description 201 of the restriction information of the changed scan parameter (step S27, YES), the controller 9 changes the setting information of the current scan parameter to a value which is not greater than the restriction items 202, 203, 204, and 205 of the menu description 201 of the restriction information of the changed scan parameter (step S28) and ends the first scan parameter restriction change process. When the setting information is not greater than the restriction items 202, 203, 204, and 205 of the menu description 201 of the restriction information of the changed scan parameter (step S27, NO), the controller 9 changes the setting information of the current scan parameter to the setting information of the scan parameter stored in the storage 11 of a case that the C mode is on (step S29) and ends the first scan parameter setting change process. When the menu description of the restriction information of the B-mode-image scan parameter is changed to OFF in step S26, the process proceeds to step S29.

Next, with reference to FIG. 9B, the scan parameter setting change process executed by the ultrasound diagnostic apparatus 100 will be described. The scan parameter setting change process is a process to manually change the setting information of the B-mode image scan parameter of a case that the C mode is on. In the ultrasound diagnostic apparatus 100, for example, the C mode is turned on in step S14 of the first ultrasound diagnostic process, and the controller 9 executes the scan parameter setting change process according to the scan parameter setting change program stored in the ROM in response to a start of an input of an operation to change the setting information of the B-mode image scan parameter from the operator via the operator 2.

As illustrated in FIG. 9B, firstly, the controller 9 finishes accepting an input of an operation to change the setting information of the B-mode image scan parameter from the operator via the operator 2 (step S31). Then, the controller 9 refers to the scan parameter restriction table 200 stored in the storage 11 and determines whether or not the setting information of the changed scan parameter, which is input in step S31, is greater than the restriction items 202, 203, 204, and 205 of the menu description 201, which is being selected and set, in the scan parameter restriction table 200 (step S32).

When the setting information is greater than the restriction items 202, 203, 204, and 205 of the menu description 201 which is being selected and set (step S32, YES), the controller 9 maintains the setting information of the scan parameter stored in the storage 11 without making a change (step S33) and ends the scan parameter setting change process. When the setting information is not greater than the restriction items 202, 203, 204, and 205 of the menu description 201 which is being selected and set (step S32, NO), the controller 9 changes the setting information of a current scan parameter to the setting information of the changed scan parameter, which is input in step S31 (step S34). Then, the controller 9 changes the setting information of the scan parameter stored in the storage 11 to the setting information of the changed scan parameter, which is changed in step S34 (step S35) and ends the scan parameter setting change process.

As described above, according to the present embodiment, the ultrasound diagnostic apparatus 100 includes: the controller 9 that sets a B-mode image scan parameter according to restriction information of a B-mode image scan parameter which affects a frame rate when the C mode is turned on and generates control information corresponding to the set scan parameter; the scan controller 10; the transmitter 3 that generates a drive signal according to the generated control information and inputs the drive signal to the ultrasound probe 101; the receiver 4 that generates reception signals of a B-mode image and a C-mode image from an electric signal generated in the ultrasound probe 101 according to the generated control information; the B-mode image generator 5 that generates B-mode image data based on the generated reception signal of the B-mode image; the C-mode image generator 7 that generates C-mode image data based on the generated reception signal of the C-mode image; and the display processing unit 8 that combines the generated B-mode image data and the generated C-mode image data and generates combined image data.

With this configuration, when combining image data of two image modes including the B mode and C mode, the frame rate of the combined image data can be easily and properly adjusted.

In addition, when the C mode is turned on and the B-mode image scan parameter is greater than the restriction information of the B-mode image scan parameter, the controller 9 changes the B-mode image scan parameter to setting information that does not exceed the restriction information and, when the C mode is turned on and the B-mode image scan parameter is not greater than the restriction information of the B-mode image scan parameter, the controller 9 does not change the B-mode image scan parameter. With this configuration, since the B-mode image scan parameter can be automatically changed according to the restriction information of the B-mode image scan parameter when the C mode is turned on, the frame rate can be properly kept high and, when the C mode is turned on, the B-mode image scan parameter does not exceed the restriction information, and the frame rate is kept high enough, the frame rate can be properly kept high without further reducing the B-mode image scan parameter.

Further, when the C mode is on, the operator 2 accepts an input to specify whether to activate the restriction information of the B-mode image scan parameter (an input to select a menu description of OFF or others (A1 to A5, B1 to B5) of the scan parameter restriction menu region 400) and, when it is specified to activate the restriction information of the B-mode image scan parameter (a selection of the menu description other than OFF is made and input), the controller 9 sets a B-mode image scan parameter which does not exceed the restriction information of the B-mode image scan parameter. With this configuration, it can be easily set whether or not to activate the restriction information of the B-mode image scan parameter, and a B-mode image scan parameter corresponding to the restriction information of the B-mode image scan parameter can be set.

Further, when the C mode is turned on, the operator 2 accepts an input to specify a degree (level) of the restriction information of the B-mode image scan parameter (an input of a selection from the menu descriptions of A1 to A5 and B1 to B5 in the scan parameter restriction menu region 400), and the controller 9 sets a B-mode image scan parameter which does not exceed the specified degree (level) of the restriction information of the B-mode image scan parameter. With this configuration, the degree (level) of the restriction information of the B-mode image scan parameter can be easily set and a B-mode image scan parameter corresponding to the restriction information of the B-mode image scan parameter can be set.

Further, when the C mode is turned on, the controller 9 stores the setting information of the B-mode image scan parameter in the B mode to the storage 11, changes the B-mode image scan parameter to the stored setting information of the scan parameter when the C mode is on and the restriction information of the B-mode image scan parameter is changed from Valid (A1 to A5, B1 to B5) to Invalid (OFF), and changes the B-mode image scan parameter to setting information which does not exceed the restriction information of the changed scan parameter when the C mode is on and the restriction information of the B-mode image scan parameter is changed from Invalid (OFF) to Valid (A1 to A5, B1 to B5). With this configuration, when the C mode is on, the states of valid and invalid of the restriction information of the B-mode image scan parameter can be easily changed. When the restriction information of the scan parameter is made invalid, the frame rate can be properly kept high without further reducing the B-mode image scan parameter and, when the restriction information of the scan parameter is made valid, the frame rate can be properly kept high by automatically changing the B-mode image scan parameter according to the restriction information of the B-mode image scan parameter.

Further, when the C mode is turned on, the controller 9 stores setting information of the B-mode image scan parameter in the B mode to the storage 11, changes the degree (level) of the restriction information of the B-mode image scan parameter when the C mode is on, changes the B-mode image scan parameter to the stored setting information of the scan parameter when the stored setting information of the can parameter is not greater than the changed degree (level) of the restriction information, and changes the B-mode image scan parameter to setting information which does not exceed the changed restriction information of the scan parameter when the stored setting information of the scan parameter is greater than the changed degree (level) of the restriction information. With this configuration, when the C mode is on, the degree (level) of the restriction information of the B-mode image scan parameter can be easily changed. When the stored setting information of the scan parameter does not exceed the changed degree (level) of the restriction information, the frame rate can be properly kept high without further reducing the B-mode image scan parameter and, when the stored setting information of the scan parameter exceeds the changed degree (level) of the restriction information, the frame rate can be properly kept high by automatically changing the B-mode image scan parameter according to the restriction information of the B-mode image scan parameter.

Further, when the C mode is turned on, the controller 9 stores the setting information of the B-mode image scan parameter in the B mode to the storage 11 and, when the C mode is turned off, the controller 9 resets the B-mode image scan parameter to the stored setting information of the B-mode image scan parameter. Thus, the B mode image data can be generated by using the image quality and frame rate of the original B-mode image in the B mode.

Further, the operator 2 accepts an input to change the B-mode image scan parameter and, when the C mode is on, the controller 9 prohibits changing the scan parameter to a B-mode image scan parameter to which a change exceeding the restriction information of the B-mode image scan parameter is input. With this configuration, it can be surely prevented that the B-mode image scan parameter is changed to a value which exceeds the restriction.

Further, when the C mode is on, the controller 9 changes the B-mode image scan parameter to a B-mode image scan parameter within a range which does not exceed its restriction information. With this configuration, it can be surely prevented that the B-mode image scan parameter is changed to a value which exceeds the restriction, and the B-mode image scan parameter can be arbitrarily changed within a range which does not exceed the restriction information.

Further, when the C mode is on and the B-mode image scan parameter is changed within a range which does not exceed the restriction information of the B-mode image scan parameter, the controller 9 updates the setting information of the B-mode image scan parameter stored in the storage 11 with a changed B-mode image scan parameter. With this configuration, it can be prevented that the B-mode image scan parameter that the operator changes is automatically reset to the original value (in the B mode before the C mode is turned on).

Further, the scan parameter is at least one of the scan density, THI of the pulse inversion method, multiple focusing, and the synthetic aperture. In the ultrasound diagnostic apparatus, these scan parameters are the parameters, which can be adjusted by the operator in general, and can be realized by a simple control. The scan parameters can be easily understood and handled by the operator.

Second Embodiment

Figure 11:
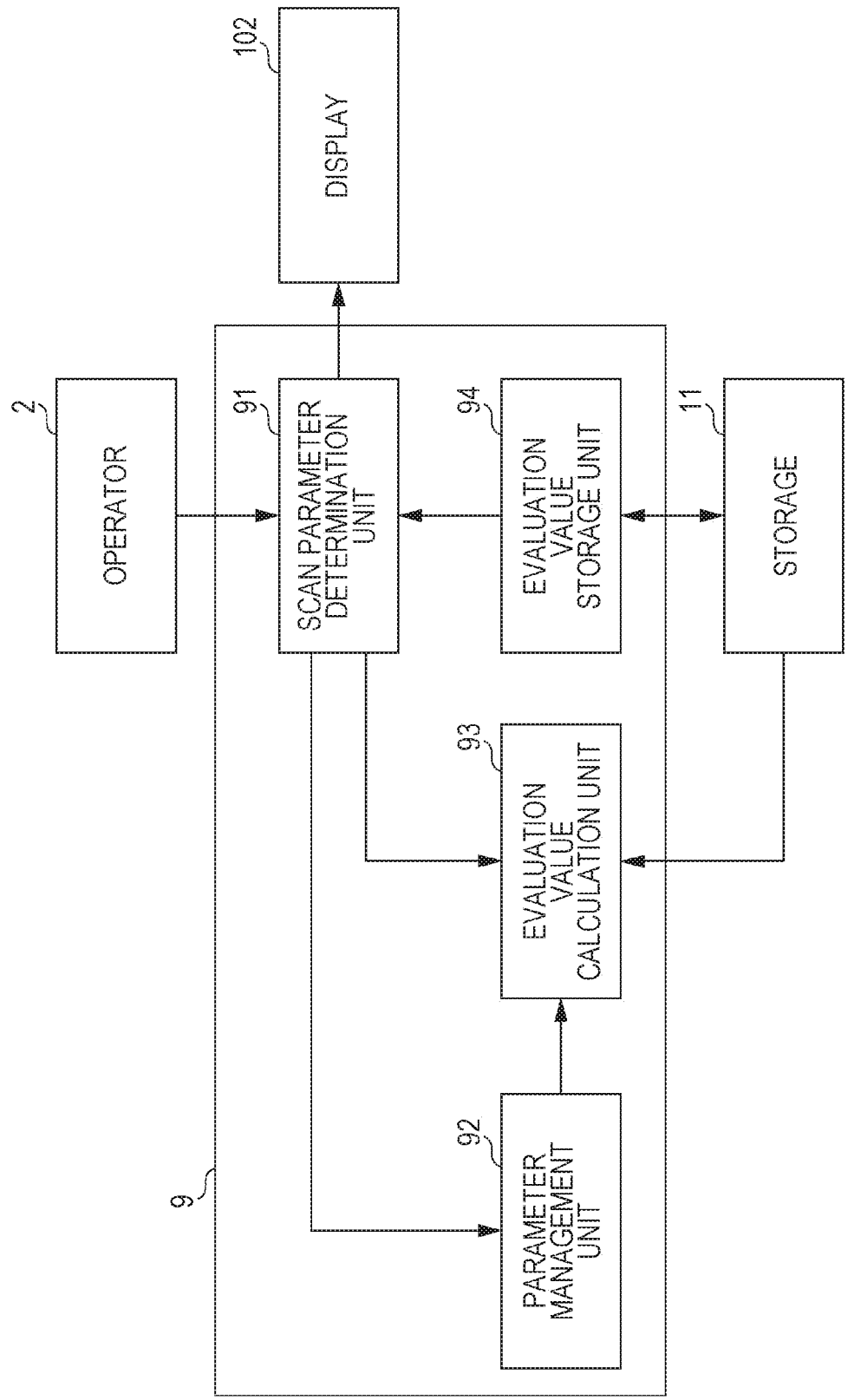
FIG. 11 is a block diagram illustrating a functional configuration of a controller according to a second embodiment.
Figure 12B:
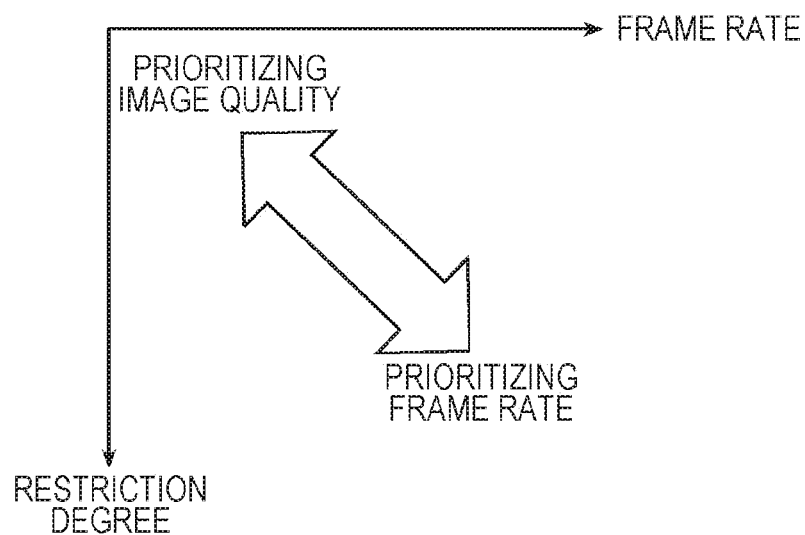
FIG. 12B is a diagram illustrating a relation between frame rates and restriction degrees.
Figure 13:
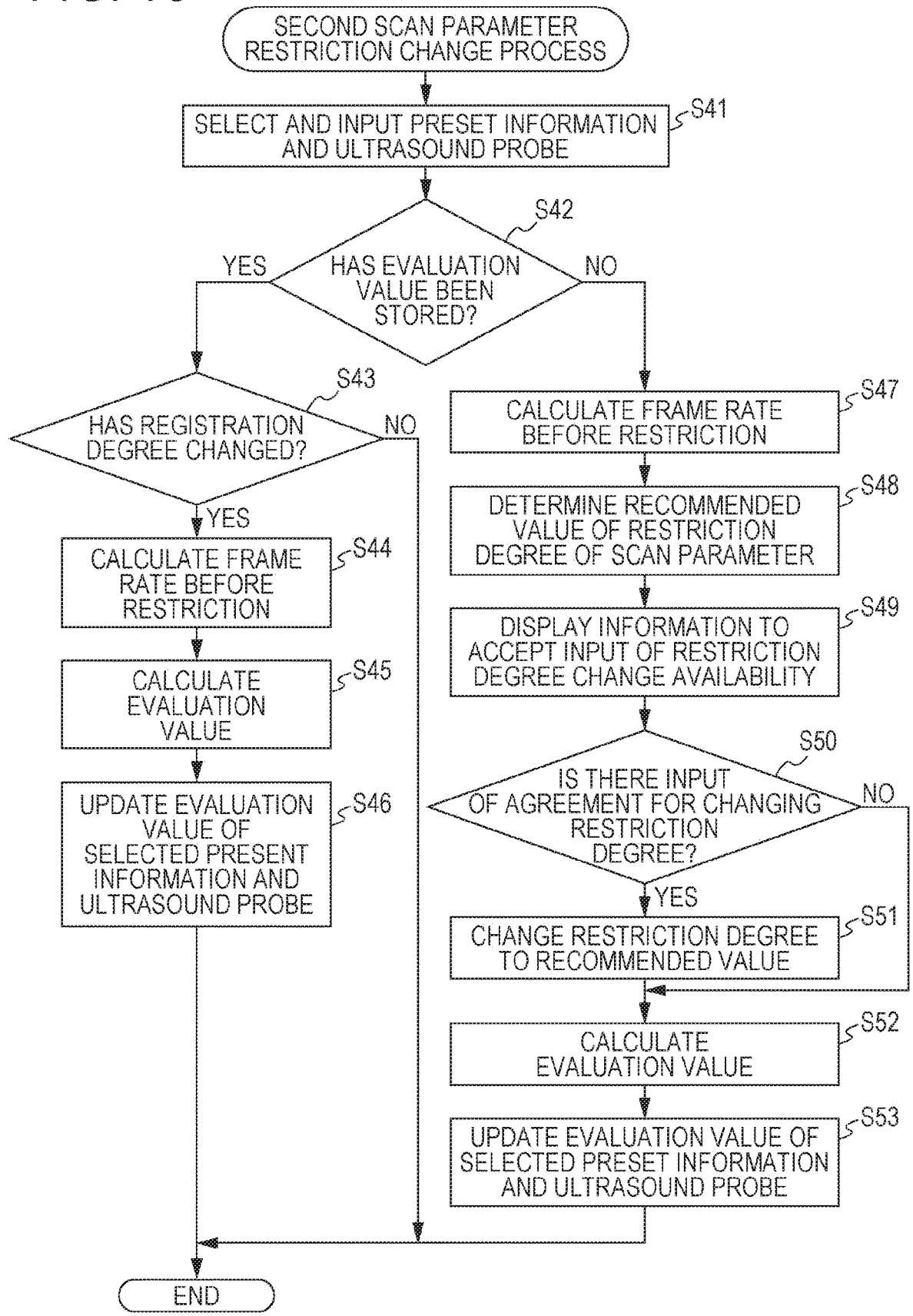
FIG. 13 is a flowchart illustrating a second scan parameter restriction change process.

With reference to FIGS. 11 to 13, a second embodiment according to the present invention will be described. FIG. 11 is a block diagram illustrating a functional configuration of a controller 9 according to the second embodiment. FIG. 12A is a diagram illustrating quantified restriction corresponding to a scan parameter restriction table 200. FIG. 12B is a diagram illustrating a relation between frame rates and restriction degrees. FIG. 13 is a flowchart illustrating a second scan parameter restriction change process.

As an apparatus configuration of the present embodiment, an ultrasound diagnostic apparatus 100 is used, similarly to the first embodiment. It is noted that a second scan parameter restriction change program is stored in the ROM of the controller 9. Further, as illustrated in FIG. 11, when a later described scan parameter restriction change process is executed, the controller 9 functions as a scan parameter determination unit 91, a parameter management unit 92, an evaluation value calculation unit 93, and an evaluation value storage unit 94.

According to the present embodiment, restriction information of a B-mode image scan parameter is automatically studied (stored) according to preset information (a diagnostic part of a test object) and an ultrasound probe 101 connected to the ultrasound diagnostic apparatus 100 as diagnostic use information. The ultrasound probe 101 connected to the ultrasound diagnostic apparatus 100 may be changed to an ultrasound probe 101 of a same type or a different type according to need. Here, a configuration in which restriction information of a B-mode image scan parameter is stored according to preset information and the ultrasound probe 101 as diagnostic use information; however, this example does not set any limitation and, for example, there may be a configuration in which the restriction information of the B-mode image scan parameter is stored according to the preset information or the ultrasound probe 101 as the diagnostic use information.

As illustrated in FIG. 12A, the restriction information of the B-mode image scan parameter is expressed as a "restriction degree (of a scan parameter)" which is quantified with 0 to 10 for example, according to the menu description 201 in the scan parameter restriction table 200. Further, as illustrated in FIG. 12B, according to the restriction degree and frame rate, an "evaluation value" that indicates whether the operator prioritizes the image quality of the B-mode image or prioritizes the frame rate is calculated and stored for each preset information and ultrasound probe 101. The stored evaluation value is used to calculate a "recommended value" which is a numerical value of a recommended restriction degree. Regarding the evaluation value, when the restriction degree used in the calculation is higher (higher restriction), the frame rate is more prioritized and, when the restriction degree used in the calculation is lower (lower restriction), the image quality of the B-mode image is more prioritized. Further, regarding the evaluation value, when the frame rate used in the calculation is higher, the frame rate is more prioritized and, when the frame rate used in the calculation is lower, the image quality of the B-mode image is more prioritized.

The scan parameter determination unit 91 accepts, via the operator 2, an input to select preset information and the ultrasound probe 101 (in a case that only one ultrasound probe 101 is being connected to the ultrasound diagnostic apparatus 100, the ultrasound probe 101 is automatically selected), and outputs the accepted input to the evaluation value calculation unit 93 and evaluation value storage unit 94.

Further, the scan parameter determination unit 91 changes the restriction degree according to an operation input to change the restriction degree. Further, the scan parameter determination unit 91 calculates a recommended value of the restriction information of the B-mode image scan parameter, requests the operator for an instruction whether to change the restriction degree by displaying information on the display 102, accepts, via the operator 2, an input of instructing whether to change the restriction degree, and controls the parameter management unit 92 to change the restriction degree to the recommended value according to the input instructing whether to change the restriction degree.

The parameter management unit 92 changes the restriction degree to the recommended value according to the instruction from the scan parameter determination unit 91. Further, the parameter management unit 92 calculates a frame rate (of the combined image data) before being restricted according to the setting information of the B-mode image scan parameter, which is not restricted, according to the instruction from the scan parameter determination unit 91. The frame rate before being restricted is used to calculate an evaluation value and it is preferable to use the frame rate before being restricted although a frame rate after being restricted may be used.

The evaluation value calculation unit 93 calculates an evaluation value with following Expression 5 by using the restriction degree and the frame rate before being restricted, which are input by the parameter management unit 92.

[evaluation value]=$a$×[frame rate]$^b$+[restriction degree]  (5)

where a is a weight constant, and b is a constant of an index set in advance.

Further, the evaluation value calculation unit 93 calculates a recommended value with following Expression 6 by using the evaluation value stored in the storage 11 as being associated with preset information and an ultrasound probe 101, which are not being selected but input from the scan parameter determination unit 91, and the frame rate before being restricted, which is input from the parameter management unit 92.

[recommended value]=[evaluation value]−$a$×[frame rate]$^b$  (6)

The evaluation value storage unit 94 stores the evaluation value calculated by the evaluation value calculation unit 93 in the storage 11 as associating with the preset information and ultrasound probe 101, which are input from the scan parameter determination unit 91 and being selected.

Next, with reference to FIG. 13, an operation by the ultrasound diagnostic apparatus 100 will be described. A second scan parameter restriction change process executed by the ultrasound diagnostic apparatus 100 will be described. The second scan parameter restriction change process is a process to change a restriction degree of setting information of a B-mode image scan parameter of a case that the C mode is on with a recommended value based on an evaluation value of the B-mode image scan parameter. In the ultrasound diagnostic apparatus 100, for example, the controller 9 executes the second scan parameter restriction change process according to a second scan parameter restriction change program stored in the ROM in response to a start of the first ultrasound diagnostic process. In this manner, the second scan parameter restriction change process is executed before step S10 of the first ultrasound diagnostic process for example.

As illustrated in FIG. 13, firstly, the scan parameter determination unit 91 accepts an input to select preset information and an ultrasound probe 101 corresponding to a diagnosis to be performed from the operator via the operator 2 (step S41). Then, the scan parameter determination unit 91 determines, via the evaluation value storage unit 94, whether an evaluation value corresponding to the selected preset information and ultrasound probe 101, which are input in step S41, are stored in the storage 11 (step S42).

When the evaluation value is stored (step S42, YES), the scan parameter determination unit 91 determines whether or not an input to change the restriction degree (for example, displaying the scan parameter restriction menu region 400 of FIG. 10, inputting to select a menu (OFF, A1 to A5, B1 to B5) by the operator, and acquiring a restriction degree corresponding to the selected menu) has been performed by the operator via the operator 2 (step S43). When the input of a restriction degree is not performed (step S43, NO), the second scan parameter restriction change process ends.

When the input of a restriction degree is performed (step S43, YES), the parameter management unit 92 calculates a frame rate before being restricted according to setting information of the B-mode image scan parameter which is not restricted upon an instruction from the scan parameter determination unit 91 (step S44). Then, the evaluation value calculation unit 93 calculates an evaluation value with Expression 5 by using the restriction degree input in step S43 and a frame rate before restriction calculated in step S44 (step S45).

Then, the evaluation value storage unit 94 updates, with the evaluation value calculated in step S45, the evaluation value, which corresponds to the selected preset information and ultrasound probe 101 and is stored in the storage 11 as being associated with the preset information and ultrasound probe 101 selected in step S41 (step S46), and ends the second scan parameter restriction change process.

When the evaluation value is not stored (step S42, NO), the parameter management unit 92 calculates a frame rate before being restricted according to the setting information of the B-mode image scan parameter, which is not restricted, according to an instruction from the scan parameter determination unit 91 (step S47). Then, the parameter management unit 92 reads an evaluation value, which does not correspond to the preset information and ultrasound probe 101 which are being selected from the storage 11, and calculates and determines a recommended value of the restriction degree with Expression 6 by using the read evaluation value and the frame rate before restriction calculated in step S47 (step S48). The evaluation value which is not corresponding to the selected preset information and ultrasound probe 101 is, for example, an evaluation value corresponding to preset information and an ultrasound probe 101, one of which is the same as the selected preset information and ultrasound probe 101, or all evaluation values stored in the storage 11. Regarding the all evaluation values stored in the storage 11, for example, an average value of the evaluation values is calculated by the parameter management unit 92 and the calculated average value of all the evaluation values is used to calculate a recommended value of a restriction degree.

Then, the scan parameter determination unit 91 displays, on the display 102, information to accept an input of a restriction degree change availability, which is used to input whether or not to change the current restriction degree with the recommended value calculated in step S48 (step S49). Then, according to the information to accept an input of a restriction degree change availability displayed in step S49, the scan parameter determination unit 91 determines whether or not operation information of an agreement with chanting the restriction degree with the recommended value calculated in step S48 is input by the operator via the operator 2 (step S50). When operation information of an agreement is input (step S50, YES), the scan parameter determination unit 91 changes the current restriction degree to the recommended value calculated in step S48 (step S51).

After step S51 or when the operation information of an agreement is not input (step S50, NO), the evaluation value calculation unit 93 calculates an evaluation value with Expression 5 by using the frame rate before restriction calculated in step S47 and the restriction degree changed in step S51, or the restriction degree which is not changed in step S50, NO (step S52).

Then, the evaluation value storage unit 94 stores the evaluation value calculated in step S52 to the storage 11 as associating with the preset information and ultrasound probe 101 being selected in step S41 (step S53) and ends the second scan parameter restriction change process. Regarding the set restriction degree, for example, in step S16 of the first ultrasound diagnostic process and step S32 of the scan parameter change setting process, the respective restriction items 202, 203, and 204 of the menu description 201 corresponding to the restriction degree are used as restriction information of a scan parameter.

As described above, according to the present embodiment, in the ultrasound diagnostic apparatus 100, the operator 2 accepts inputs of preset information and an ultrasound probe 101 which are associated with the B-mode image scan parameter, and a restriction degree indicating a degree of restriction information of the B-mode image scan parameter, and the controller 9 calculates an evaluation value that indicates whether to prioritize the image quality of the B-mode image or prioritize the frame rate by using the input restriction degree and frame rate and stores the calculated evaluation value to the storage 11 as associating with the input preset information and ultrasound probe 101. When preset information and an ultrasound probe 101 corresponding to an evaluation value, which is not stored in the storage 11, are input, the controller 9 calculates a recommended value of a restriction degree of the B-mode image scan parameter by using an evaluation value and a frame rate, which corresponds to another preset information and ultrasound probe 101 of the input preset information and ultrasound probe 101, and sets a restriction degree according to the calculated recommended value. With this configuration, a restriction degree whether the operator would prioritize the image quality of the B mode or prioritize the frame rate is automatically studied, and a restriction degree can be set according to the operator's preference without setting manually, even with different preset information and an ultrasound probe 101 which are not selected.

Further, regarding the evaluation value, when the restriction degree used in the calculation is higher, the frame rate is prioritized and, when the restriction degree used in the calculation is lower, the image quality of the B-mode image is prioritized. Further, regarding the evaluation value, the frame rate used in the calculation is higher, the frame rate is more prioritized and, when the frame rate used in the calculation is lower, the image quality of the B-mode image is more prioritized.

Further, the operator 2 accepts information input whether a change of the restriction degree to the calculated recommended value is available, and the controller 9 changes the restriction degree to the calculated recommended value according to an input of an agreement for changing the restriction degree and does not change the restriction degree to the calculated a recommended value according to an input to prohibit the change of the restriction degree. With this configuration, it can be prevented that a recommended value based on a study result is automatically reflected to the restriction degree of the scan parameter.

Further, when the preset information and ultrasound probe 101 corresponding to an evaluation value which is not store din the storage 11 are input, the controller 9 uses an average value of evaluation values corresponding to the all preset information and ultrasound probe 101 stored in the storage 11 or an evaluation value corresponding to the preset information and ultrasound probe 101 one of which is the same as the preset information and ultrasound probe 101 which are input and stored in the storage 11, as different preset information and ultrasound probe 101 from the input preset information and ultrasound probe 101. With this configuration, a recommended value can be calculated by using an evaluation value corresponding to different proper preset information and ultrasound probe 101.

The above description has described an example in which a ROM is used as a computer readable medium of a program according to the present invention; however, the present invention is not limited by this example.

As another computer-readable medium, a non-volatile memory such as a flash memory, and a portable recording medium such as a CD-ROM may be used.

Further, as a medium for providing program data according to the present invention via a communication line, a carrier wave may be applied to the present invention.

Here, according to the description of the above embodiments is an example of a preferable ultrasound diagnostic apparatus, an ultrasound diagnostic image generating method and a program according to the present invention and the present invention is not limited to this example.

For example, according to the above embodiments, there may be a configuration in which the first and second embodiments are combined according to need.

Further, the respective embodiments have described configurations in which the B-mode image data as a first image mode and C-mode image data in a C (color flow) mode including a color Doppler mode and a power Doppler mode as a second image mode are combined; however, this example does not set any limitation. There may be a configuration in which the B mode image data and different image data in a second image mode such as tissue Doppler imaging (2D-TDI) and elastography mode as the second image mode are combined.

Further, modifications may be applied to specific configurations and specific operations of the respective units composing the ultrasound diagnostic apparatus 100 according to the above embodiments within a scope of the present invention according to need.

Although embodiments of the present invention have been described and illustrated in detail, it is clearly understood that the same is by way of illustration and example only and not limitation, the scope of the present invention should be interpreted by terms of the appended claims.

What is claimed is:

1. An ultrasound diagnostic apparatus that can combine image data and has a first image mode and a second image mode, the ultrasound diagnostic apparatus comprising:
   a hardware processor that sets a scan parameter for scanning in a first image mode according to restriction information of the scan parameter for scanning in the first image mode, which affects a frame rate, when the second image mode is turned on and generates control information corresponding to the set scan parameter;
   an operator that receives an input, wherein the restriction information is input to the operator when the second image mode is turned on;
   a transmitter that generates a drive signal according to the generated control information and inputs the drive signal to an ultrasound probe that transmits transmission ultrasound to a test object according to the drive signal;
   a receiver that generates a reception signal of the images in the first and second image modes from an electric signal generated in the ultrasound probe in response to reflected ultrasound, according to the generated control information;
   a first-image-mode image generator that generates first-image-mode image data based on the generated reception signal of the image of the first image mode;
   a second-image-mode image generator that generates second-image-mode image data based on the generated reception signal of the image in the second image mode; and
   a combiner that generates combined image data by combining the generated first-image-mode image data and the generated second-image-mode image data,
   wherein the hardware processor stores the setting information of the scan parameter for scanning in the first image mode to a first storage when the second image mode is turned on, and resets the scan parameter for scanning in the first image mode to the stored setting information of the scan parameter for scanning in the first image mode when the second image mode is turned off.

2. The ultrasound diagnostic apparatus according to claim 1, wherein
   the hardware processor
   changes the scan parameter for scanning in the first image mode to setting information that does not exceed the restriction information when the second image mode is turned on and the scan parameter of the image of the first image mode exceeds the restriction information of the scan parameter for scanning in the first image mode, and
   does not change the scan parameter for scanning in the first image mode when the second image mode is turned on and the scan parameter of the image of the first image mode does not exceed the restriction information of the scan parameter of the image of the first image mode.

3. The ultrasound diagnostic apparatus according to claim 1, wherein
   the operator accepts an input specifying whether or not to activate the restriction information of the scan parameter for scanning in the first image mode when the second image mode is on, and
   when it is specified to activate the restriction information of the scan parameter for scanning in the first image mode, the hardware processor sets a scan parameter for scanning in the first image mode which does not exceed the restriction information of the scan parameter for scanning in the first image mode.

4. The ultrasound diagnostic apparatus according to claim 3, wherein
   when the second image mode is on, the operator accepts an input specifying a degree of the restriction information of the scan parameter for scanning in the first image mode, and
   when it is specified to activate the restriction information of the scan parameter for scanning in the first image mode, the hardware processor sets a scan parameter of the image of the first image mode which does not exceed the specified degree of the restriction information of the scan parameter for scanning in the first image mode.

5. The ultrasound diagnostic apparatus according to claim 1, wherein the operator accepts a specification of a degree of the restriction information of the scan parameter for scanning in the first image mode when the second image mode is on, wherein the hardware processor sets a scan parameter for scanning in the first image mode which does not exceed the specified degree of the restriction information of the scan parameter for scanning in the first image mode.

6. The ultrasound diagnostic apparatus according to claim 3, wherein the hardware processor stores setting information of the scan parameter for scanning in the first image mode to a first storage when the second image mode is turned on, changes the scan parameter for scanning in the first mode to the stored setting information of the scan parameter when the second image mode is on and the restriction information of the scan parameter for scanning in the first image mode is switched from an active state to an inactive state, and changes the scan parameter for scanning in the first image mode to setting information which does not exceed the changed restriction information of the scan parameter when the second image mode is on and restriction information of the scan parameter for scanning in the first image mode is switched from the inactive state to the active state.

7. The ultrasound diagnostic apparatus according to claim 4, wherein the hardware processor stores the setting information of the scan parameter for scanning in the first image mode to a first storage when the second image mode is turned on, accepts a change of the degree of the restriction information of the scan parameter for scanning in the first image mode when the second image mode is on, changes the scan parameter for scanning in the first image mode to the stored setting information of the scan parameter when the stored setting information of the scan parameter does not exceed the changed degree of the restriction information, and changes the scan parameter for scanning in the first image mode to the setting information which does not exceed the changed restriction information of the scan parameter when the stored setting information of the scan parameter exceeds the changed degree of the restriction information.

8. The ultrasound diagnostic apparatus according to claim 1, wherein the operator accepts an input to change the scan parameter to a new scan parameter for scanning in the first image mode, wherein when the second image mode is on, the hardware processor prohibits changing the scan parameter to the new scan parameter for scanning in the first image mode when the new scan parameter exceeds the restriction information of the scan parameter of the image of for scanning in the first image mode.

9. The ultrasound diagnostic apparatus according to claim 8, wherein when the second image mode is on, the hardware processor changes the scan parameter to the new scan parameter for scanning in the first image mode when the new scan parameter does not exceed the restriction information of the scan parameter for scanning in the first image mode.

10. The ultrasound diagnostic apparatus according to claim 1, wherein when the second image mode is on and the scan parameter for scanning in the first image mode is changed within a range which does not exceed the restriction information of the scan parameter for scanning in the first image mode, the hardware processor updates the stored setting information of the scan parameter for scanning in the first image mode with the changed scan parameter of the image of the first image mode.

11. The ultrasound diagnostic apparatus according to claim 1, wherein the scan parameter is at least one of a scan density, THI of a pulse inversion method, multiple focusing, and a synthetic aperture.

12. The ultrasound diagnostic apparatus according to claim 1, wherein the operator accepts an input of diagnostic use information that is associated with the scan parameters for scanning in the first image mode and a restriction degree that indicates a degree of the restriction information of the scan parameter for scanning in the first image mode, wherein the hardware processor calculates an evaluation value that indicates whether to prioritize an image quality in the first image mode or prioritize a frame rate by using the input restriction degree and a frame rate, stores the calculated evaluation value to a second storage as associating with the input diagnostic use information, calculates a recommended value of the restriction degree of the scan parameter for scanning in the first image mode by using the evaluation value and frame rate corresponding to diagnostic use information which is different from the input diagnostic use information when the diagnostic use information corresponding to an evaluation value which is not stored in the second storage is input, and sets a restriction degree according to the calculated recommended value.

13. The ultrasound diagnostic apparatus according to claim 12, wherein regarding the evaluation value, when a restriction degree used in the calculation is higher, the frame rate is prioritized and, when the restriction degree used in the calculation is lower, the image quality for scanning in the first image mode is prioritized.

14. The ultrasound diagnostic apparatus according to claim 12, wherein regarding the evaluation value, when the frame rate used in the calculation is faster, the frame rate is prioritized and, when the frame rate used in the calculation is slower, the image quality for scanning in the first image mode is prioritized.

15. The ultrasound diagnostic apparatus according to claim 12, wherein the operator accepts an input of information that indicates availability of a change of the restriction degree to the calculated recommended value, and the hardware processor changes the restriction degree to the calculated recommended value according to an input of agreement for changing the restriction degree, and does not change the restriction degree to the calculated recommended value according to an input to prohibit changing the restriction degree.

16. The ultrasound diagnostic apparatus according to claim 12, wherein when diagnostic use information corresponding to an evaluation value which is not stored in the second storage is input, the hardware processor uses, as diagnostic use information different from the input diagnostic use information, an average value of all evaluation values corresponding to diagnostic use information stored in the second storage or an evaluation value corresponding to the diagnostic use information including a piece of information which is the same as the input diagnostic use information stored in the second storage.

17. The ultrasound diagnostic apparatus according to claim 12, wherein
the diagnostic use information is at least one of preset information and an ultrasound probe.

18. The ultrasound diagnostic apparatus according to claim 1, wherein
the first image mode is a B mode, and
the second image mode is a color Doppler mode, a power Doppler mode, tissue Doppler imaging or an elastography mode.

19. An ultrasound diagnostic image generating method that can combine image data and uses a first image mode and a second image mode, the method comprising:
setting a scan parameter for scanning in a first image mode according to restriction information of the scan parameter for scanning in the first image mode that affects a frame rate and generating control information according to the set scan parameters when the second image mode is on;
inputting the restriction information to an operator when the second image mode is turned on;
generating a drive signal according to the generated control information and inputting the drive signal to an ultrasound probe that transmits transmission ultrasound to a test object according to the drive signal and receives reflected ultrasound;
generating reception signals of images of the first and second image modes from an electric signal generated in the ultrasound probe, according to the generated control information;
generating first-image-mode image data based on the generated reception signal of the image of the first image mode;
generating second-image-mode image data based on the generated reception signal of the image of the second image mode;
generating combined image data by combining the generated first-image-mode image data and the generated second-image-mode image data;
storing the setting information of the scan parameter for scanning in the first image mode to a first storage when the second image mode is turned on; and
resetting the scan parameter for scanning in the first image mode to the stored setting information of the scan parameter for scanning in the first image mode when the second image mode is turned off.

20. A non-transitory recording medium storing a computer readable program causing a computer of an ultrasound diagnostic apparatus that can combine image data and has a first image mode and a second image mode to function as:
a hardware processor that sets a scan parameter for scanning in a first image mode according to restriction information of the scan parameter for scanning in the first image mode, which affects a frame rate, when the second image mode is turned on and generates control information corresponding to the set scan parameter;
an operator that receives an input, wherein the restriction information is input to the operator when the second image mode is turned on;
a transmitter that generates a drive signal according to the generated control information and inputs the drive signal to an ultrasound probe that transmits transmission ultrasound to a test object according to the drive signal;
a receiver that generates a reception signal of the images in the first and second image modes from an electric signal generated in the ultrasound probe in response to reflected ultrasound, according to the generated control information;
a first-image-mode image generator that generates first-image-mode image data based on the generated reception signal of the image of the first image mode;
a second-image-mode image generator that generates second-image-mode image data based on the generated reception signal of the image in the second image mode;
a combiner that generates combined image data by combining the generated first-image-mode image data and the generated second-image-mode image data;
storing the setting information of the scan parameter for scanning in the first image mode to a first storage when the second image mode is turned on; and
resetting the scan parameter for scanning in the first image mode to the stored setting information of the scan parameter for scanning in the first image mode when the second image mode is turned off.

21. The ultrasound diagnostic apparatus according to claim 1, wherein
the operator receives the input from a user, and the restriction information is input to the operator by the user.

* * * * *